(12) United States Patent
Forssmann et al.

(10) Patent No.: US 7,045,594 B1
(45) Date of Patent: May 16, 2006

(54) SERINE PROTEINASE INHIBITORS

(75) Inventors: Wolf-Georg Forssmann, Hannover (DE); Hans-Jürgen Magert, Hannover (DE); Ludger Ständker, Hannover (DE); Peter Kreuztmann, Magdeburg (DE)

(73) Assignee: Pharis Biotec GmbH, Hannover (DE)

( * ) Notice: Subject to any disclaimer, the term of this patent is extended or adjusted under 35 U.S.C. 154(b) by 0 days.

(21) Appl. No.: 09/582,328

(22) PCT Filed: Dec. 23, 1998

(86) PCT No.: PCT/EP98/08424

§ 371 (c)(1),
(2), (4) Date: Jul. 19, 2000

(87) PCT Pub. No.: WO99/33974

PCT Pub. Date: Jul. 8, 1999

(30) Foreign Application Priority Data

Dec. 23, 1997 (DE) ................. 197 57 572
Jan. 8, 1998 (DE) ................. 198 00 363

(51) Int. Cl.
*C07K 14/00* (2006.01)
*A61K 38/00* (2006.01)

(52) U.S. Cl. ................... 530/350; 530/300; 514/12

(58) Field of Classification Search ............... 435/69.2; 530/350, 300; 514/12
See application file for complete search history.

(56) References Cited

U.S. PATENT DOCUMENTS

2003/0055236 A1* 3/2003 Moore et al. ............... 536/23.2

FOREIGN PATENT DOCUMENTS

| EP | 0300459 | 1/1989 |
|----|---------|--------|
| WO | WO9502055 | 1/1995 |
| WO | WO9715670 | 5/1997 |

OTHER PUBLICATIONS

Hanh et al., "Characterization of comE, a late competence operon of *Bacilus subtilis* required for the binding and uptake of transforming DNA", 1993, 10(1), 99-111.*

* cited by examiner

*Primary Examiner*—Robert A. Wax
*Assistant Examiner*—Suzanne M. Mayer
(74) *Attorney, Agent, or Firm*—Jacobson Holman PLLC

(57) ABSTRACT

A serine protease inhibitor, characterized by having a domain with four cysteines, and a sequence of 0 to 20 amino acids is present between the first and second cysteines, or the serine protease inhibitor has a domain with six cysteines, and a sequence of 7 to 20 amino acids is present between the first and second cysteines.

11 Claims, 6 Drawing Sheets

FIG. 1

VAKTI-1 cDNA and its translation into amino acid sequence

```
                                                              M   K   I   A
Frame 2  ATG CAT GGA GTG GAC CTG TAG GCG ACT TGC ATC GTC TTC AAC ATG AAG ATA GCC
             10          19          28          37          46          55

I——MEMC-1—>
                                                           I—>HF6479
          T   V   S   V   L   L   P   L   A   L   C   L   I   Q   D   A   A   S   I   K   N
         ACA GTG TCA GTG CTT CTG CCC TTG GCT CTT TGC CTC ATA CAA GAT GCT GCC AGT AAG AAT
                 64          73          82          91         100         109

———MEMC-1———>     ————CHEF-1————>
          E   D   Q   E   M   C   H   E   F   Q   A   F   M   K   N   G   K   L   F   C
         GAA GAT CAG GAA ATG TGC CAT GAA TTT CAG GCA TTT ATG AAA AAT GGA AAA CTG TTC TGT
                124         133         142         151         160         169

<————————————CHEF-14————————
              —————————————CHEF-11————————>                    <—CHEF-2—
          P   Q   D   K   K   F   F   Q   S   L   D   G   I   M   F   I   N   K   C   A
         CCC CAG GAT AAG AAA TTT TTT CAA AGT CTT GAT GGA ATA ATG TTC ATC AAT AAA TGT GCC
                184         193         202         211         220         229

<———CHEF-2———                       HF6479<———I
          T   C   K   M   I   L   E   K   E   A   K   S   Q   K   R   A   R   H   L   A
         ACG TGC AAA ATG ATA CTG GAA AAA GAA GCA AAA TCA CAG AAG AGG GCC AGG CAT TTA GCA
                244         253         262         271         280         289

R   A   P   K   A   T   A   P   T   E   L   N   C   D   D   F   K   K   G   E
         AGA GCT CCC AAG GCT ACT GCC CCA ACA GAG CTG AAT TGT GAT GAT TTT AAA AAA GGA GAA
                304         313         322         331         340         349

R   D   G   D   F   I   C   P   D   Y   Y   E   A   V   C   G   T   D   G   K
         AGA GAT GGG GAT TTT ATC TGT CCT GAT TAT TAT GAA GCT GTT TCT GGC ACA GAT GGG AAA
                364         373         382         391         400         409

T   Y   D   N   R   C   A   L   C   A   E   N   A   K   T   G   S   Q   I   G
         ACA TAT GAC AAC AGA TGT GCA CTG TGT GCT GAG AAT GCG AAA ACC GGG TCC CAA ATT GGT
                424         433         442         451         460         469

V   K   S   E   G   E   C   K   S   S   N   P   E   Q   V   R   S   I   V   S
         GTA AAA AGT GAA GGG GAA TGT AAG AGC AGT AAT CCA GAG CAG GTG AGG TCA ATT GTC AGC
                484         493         502         511         520         529

L   M   G   N   T   G   R   L   T   S   N   S   K STOP
         CTG ATG GGA AAT ACT GGG AGG CTA ACT TCA AAT AGT AAG TAG GTG CTG TCC TCT TCC TTC
                544         553         562         571         580         589

TTA GGT GGG AGC CTT GGA AGG AAT TAA TTC TTG CTT TAT GTG AAA TGG AAT ACC CAG TTA
                604         613         622         631         640         649

CTG CCC ACT AAT ATG AAA AAG CTA ATT ATA GTC TCT GAA ACT GGA TCA GAT TAC TTT GGT
                664         673         682         691         700         709

GGT TAA GAT CTT TCA ATC TAT TGC TGC TTT GTA  T
                724         733         742         749
```

VAKTI-2 cDNA and its translation into amino acid sequence

FIG. 2A

Frame 2

```
                                                          M   K   I   A
ATG CAT GGA GTG GAG CTG TAG CCG ACT TGC ATC ATG TTG AAC ATG AAG ATA GCC
        10          19          28          37          46          55
                                                              |—> HF 6479
 T   V   S   V   L   L   P   L   A   L   C   L   I   Q   D   A   A   S   I   K   N
ACA GTG TCA GTG CTT CTG CCC TTG GCT CTT TGC CTC ATA CAA GAT GCT GCC AGT AAG AAT
        64          73          82          91         100         109
                Repeat 1                                                      #
 E   D   Q   E   M   C   H   E   F   Q   M   F   M   K   N   G   K   L   F   C
GAA GAT CAG GAA ATG TGC CAT GAA TTT CAG GCA TTT ATG AAA AAT GGA AAA CTG TTC TGT
       124         133         142         151         160         169
                                                                          #
 P   Q   D   K   K   F   F   Q   S   L   D   G   I   M   F   I   N   K   C   A
CCC CAG GAT AAG AAA TTT TTT CAA AGT CTT GAT GGA ATA ATG TTC ATC AAT AAA TGT GCC
       184         193         202         211         220         229
                                HF 6479<—|
 T   C   K   M   I   L   E   K   E   A   K   S   Q   K   R   A   R   H   L   A
ACG TGC AAA ATG ATA CTG GAA AAA GAA GCA AAA TCA CAG AAG AGG GCC AGG CAT TTA GCA
       244         253         262         271         280         289
                                            typical Kazal domain
 R   A   P   K   A   T   A   P   T   E   L   N   C   D   D   F   K   K   G   E
AGA GCT CCC AAG GCT ACT GCC CCA ACA GAG CTG AAT TGT GAT GAT TTT AAA AAA GGA GAA
       304         313         322         331         340         349
                         #                                     +
 R   D   G   D   F   I   C   P   D   Y   Y   E   A   V   C   G   T   D   G   K
AGA GAT GGG GAT TTT ATC TGT CCT GAT TAT TAT GAA GCT GTT TGT GGC ACA GAT GGG AAA
       364         373         382         391         400         409
         !               #           *
 T   Y   D   N   R   C   A   L   C   A   E   N   A   K   T   G   S   Q   I   G
ACA TAT GAC AAC AGA TGT GCA CTG TGT GCT GAG AAT GCG AAA ACC GGG TCC CAA ATT GGT
       424         433         442         451         460         469
                                                            Repeat 2
 V   K   S   E   G   E   C   K   S   S   N   P   E   Q   D   V   C   S   A   F
GTA AAA AGT GAA GGG GAA TGT AAG AGC AGT AAT CCA GAG CAG GAT GTA TGC AGT GCT TTT
       484         493         502         511         520         529
                                             *
 R   P   F   V   R   N   G   R   L   G   C   T   R   E   N   D   P   V   L   G
CGG CCC TTT GTT AGA AAT GGA AGA CTT GGA TGC ACA AGG GAA AAT GAT CCT GTT CTT GGT
       544         553         562         571         580         589
                                    #           *
 P   D   G   K   T   H   G   N   K   C   A   M   C   A   E   L   F   L   K   E
CCT GAT GGG AAG ACG CAT GGC AAT AAG TGT GCA ATG TGT GCT GAG CTG TTT TTA AAA GAA
       604         613         622         631         640         649

A   E   N   A   K   R   E   G   E   T   R   I   R   R   N   A   E   K   D   F
GCT GAA AAT GCC AAG CGA GAG GGT GAA ACT AGA ATT CGA CGA AAT GCT GAA AAG GAT TTT
       664         673         682         691         700         709
Repeat 3                                                       #
 C   K   E   Y   E   K   Q   V   R   N   G   R   L   F   C   T   R   E   S   D
TGC AAG GAA TAT GAA AAA CAA GTG AGA AAT GGA AGG CTT TTT TGT ACA CGG GAG AGT GAT
       724         733         742         751         760         769
                                                       #
 P   V   R   G   P   D   G   R   M   H   G   N   K   C   A   L   C   A   E   I
CCA GTC CGT GGC CCT GAC GGC AGG ATG CAT GGC AAC AAA TGT GCC CTG TGT GCT GAA ATT
       784         793         802         811         820         829

F   K   R   R   F   S   E   E   N   S   K   T   D   Q   N   L   G   K   A   E
TTC AAG CGG CGT TTT TCA GAG GAA AAC AGT AAA ACA GAT CAA AAT TTG GGA AAA GCT GAA
       844         853         862         871         880         889
```

FIG. 2B

```
                                                              Repeat 4
  E   K   T   K   V   K   R   E   I   V   K   L   C   S   Q   Y   Q   N   Q   A
 GAA AAA ACT AAA GTT AAA AGA GAA ATT GTC AAA CTC TGC AGT CAA TAT CAA AAT CAG GCA
         904         913         922         931         940         949

K   N   G   I   L   F   C   T   R   E   N   D   P   I   R   G   P   D   G   K
 AAG AAT GGA ATA CTT TTC TGT ACC AGA GAA AAT GAC CCT ATT CGT GGT CCA GAT GGG AAA
         964         973         982         991        1000        1009

M   H   G   N   L   C   S   M   C   Q   V   Y   F   Q   A   E   N   E   E   M
 ATG CAT GGC AAC TTG TGT TCC ATG TGT CAA GTC TAC TTC CAA GCA GAA AAT GAA GAA GCG
        1024        1033        1042        1051        1060        1069

|---->HF7665
  K   K   A   E   A   R   A   R   N   K   R   I   E   S   G   K   A   T   S   Y   A
 AAA AAG GCT GAA GCA CGA GCT AGA AAC AAA AGA GAA TCT GGA AAA GCA ACC TCA TAT GCA
        1084        1093        1102        1111        1120        1129

Repeat 5
  E   L   C   N   E   Y   R   K   L   V   R   N   G   K   L   A   C   T   R   E
 GAG CTT TGC AAT GAA TAT CGA AAG CTT GTG AGG AAC GGA AAA CTT GCT TGC ACC AGA GAG
        1144        1153        1162        1171        1180        1189

N   D   P   I   Q   G   P   D   G   K   V   H   G   N   T   C   S   M   C   E
 AAC GAT CCT ATT CAG GGC CCA GAT GGG AAA GTG CAC GGC AAC ACC TGC TCC ATG TGT GAG
        1204        1213        1222        1231        1240        1249

HF7665<----|
  V   F   F   Q   A   E   E   E   E   K   K   K   K   E   G   E   S   R   N   I   K
 GTT TTT TTC CAA GCA GAA GAA GAA GAA AAG AAA AAG AAG GAA GGC GAA TOA AGA AAC AAA
        1264        1273        1282        1291        1300        1309

Repeat 6
  R   Q   S   K   S   T   A   S   F   E   E   L   C   S   E   Y   R   K   S   R
 AGA CAA TCT AAG AGT ACA GCT TCC TTT GAG GAG TTG TGT AGT GAA TAC CGC AAA TCC AGG
        1324        1333        1342        1351        1360        1369

K   N   G   R   L   F   C   T   R   E   N   D   P   I   Q   G   P   D   G   K
 AAA AAC GGA CGG CTT TTT TGC ACC AGA GAG AAT GAC CCC ATC CAG GGC CCA GAT GGG AAA
        1384        1393        1402        1411        1420        1429

M   H   G   N   T   C   S   M   C   E   A   F   F   Q   Q   E   E   R   A   R
 ATG CAT GGC AAC ACC TGC TCC ATG TGT GAG GCC TTC TTT CAA CAA GAA GAA AGA GCA AGA
        1444        1453        1462        1471        1480        1489

Repeat 7
  A   K   A   K   R   E   A   A   K   E   I   C   S   E   F   R   D   Q   V   R
 GCA AAG GCT AAA AGA GAA GCT GCA AAG GAA ATC TGC AGT GAA TTT CGG GAC CAA GTG AGG
        1504        1513        1522        1531        1540        1549

N   G   T   L   I   C   T   R   E   H   N   P   V   R   G   P   D   G   K   M
 AAT GGA ACA CTT ATA TGC ACC AGG GAG CAT AAT CCT GTC CGT GGA CCA GAT GGC AAA ATG
        1564        1573        1582        1591        1600        1609

H   G   N   K   C   A   M   C   A   S   V   F   K   L   E   E   E   E   K   K
 CAT GGA AAC AAG TGT GCC ATG TGT GCC AGT GTG TTC AAA CTT GAA GAA GAA GAG AAG AAA
        1624        1633        1642        1651        1660        1669

N   D   K   E   E   K   G   K   V   E   A   E   K   V   K   R   E   A   V   Q
 AAT GAT AAA GAA GAA AAA GGG AAA GTT GAG GCT GAA AAA GTT AAG AGA GAA GCA GTT CAG
        1684        1693        1702        1711        1720        1729

Repeat 8
  E   L   C   S   E   Y   R   H   Y   V   R   N   G   R   L   P   C   T   R   E
 GAG CTG TGC AGT GAA TAT CGT CAT TAT GTC AGG AAT GGA CGA CTC CCC TGT ACC AGA GAC
        1744        1753        1762        1771        1780        1789
```

FIG. 2C

```
 N   D   P   I   E   G   L   D   G   K   I   H   G   N   T   C   S   M   C   E
AAT GAT CCT ATT GAG GGT CTA GAT GGG AAA ATC CAC GGC AAC ACC TGC TCC ATG TGT GAA
        1804        1813        1822        1831        1840        1849

A   F   F   Q   Q   E   A   K   E   K   E   R   A   E   P   R   A   K   V   K
GCC TTC TTC CAG CAA GAA GCA AAA GAA AAA GAA AGA GCT GAA CCC AGA GCA AAA GTC AAA
        1864        1873        1882        1891        1900        1909
```

Repeat 9

```
 R   E   A   E   K   E   T   C   D   E   F   R   R   L   L   Q   N   G   K   L
AGA GAA GCT GAA AAG GAG ACA TGC GAT GAA TTT CGG AGA CTT TTG CAA AAT GGA AAA CTT
        1924        1933        1942        1951        1960        1969

F   C   T   R   E   N   D   P   V   R   G   P   D   G   K   T   H   G   N   K
TTC TGC ACA AGA GAA AAT GAT CCT GTG CGT GGC CCA GAT GGC AAG ACC CAT GGC AAC AAG
        1984        1993        2002        2011        2020        2029

C   A   M   C   K   A   V   F   Q   K   E   N   E   E   R   K   R   K   E   E
TGT GCC ATG TGT AAG GCA GTC TTC CAG AAA GAA AAT GAG GAA AGA AAG AGG AAA GAA GAG
        2044        2053        2062        2071        2080        2089

E   D   Q   R   N   A   A   G   H   G   S   S   G   G   G   G   N   T   Q
GAA GAT CAG AGA AAT GCT GCA GGA CAT GGT TCC AGT GGT GGT GGA GGA AAC ACT CAG
        2104        2113        2122        2131        2140        2149
```

Repeat 10

```
 D   E   C   A   E   Y   R   E   Q   M   K   N   G   R   L   S   C   T   R   E
GAC GAA TGT GCT GAG TAT CGG GAA CAA ATG AAA AAT GGA AGA CTC AGC TGT ACT CGG GAG
        2164        2173        2182        2191        2200        2209

S   D   P   V   R   D   A   D   G   K   S   Y   N   N   Q   C   T   M   C   K
AGT GAT CCT GTA CGT GAT GCT GAT GGC AAA TCG TAC AAC AAT CAG TGT ACC ATG TGT AAA
        2224        2233        2242        2251        2260        2269

A   K   L   E   R   E   A   E   R   K   N   E   Y   S   R   S   R   S   N   G
GCA AAA TTG GAA AGA GAA GCA GAG AGA AAA AAT GAG TAT TCT CGC TCC AGA TCA AAT GGG
        2284        2293        2302        2311        2320        2329
```

Repeat 11

```
 T   G   S   E   S   G   K   D   T   C   D   E   F   R   S   Q   M   K   N   G
ACT GGA TCA GAA TCA GGG AAG GAT ACA TGT GAT GAG TTT AGA AGC CAA ATG AAA AAT GGA
        2344        2353        2362        2371        2380        2389

K   L   I   C   T   R   E   S   D   P   V   R   G   P   D   G   K   T   H   G
AAA CTT ATC TGC ACT CGA GAA AGT GAC CCT GTC CGG GGT CCA GAT GGC AAG ACA CAT GGT
        2404        2413        2422        2431        2440        2449

N   K   C   T   M   C   K   E   K   L   E   M   E   A   A   E   K   K   R   K
AAT AAG TGT ACT ATG TGT AAG GAA AAA CTG GAA AGG GAA GCA GCT GAA AAA AAA AGA AAG
        2464        2473        2482        2491        2500        2509

R   M   K   T   G   A   I   Q   E   K   G   A   I   Q   E   K   G   A   M   T
AGG ATG AAG ACA GGA GCA ATA CAG GAG AAA GGA GCA ATA CAG GAG AAA GGA GCA ATG ACA
        2524        2533        2542        2551        2560        2569

K   R   I   C   V   V   N   F   E   A   C   R   E   M   E   S   L   S   A   P
ATG AGG ATC TGT GTC GTC AAT TTC GAA GCA TGC AGA GAA ATG GAA AGC TTA TCT GCA CCA
        2584        2593        2602        2611        2620        2629
```

FIG. 2D

```
          E   K   I   T   L   F   E   A   H   M   A   R   C   T   S   I   N   V   L   C
         GAG AAA ATA ACC CTG TTC GAG GCC CAT ATG GCA AGA TGC ACA TCA ATA AAT GTG CTA TGT
             2644        2653        2662        2671        2680        2689

V   R   A   S   L   I   E   K   L   M   K   E   R   K   M   K   R   N   Q
         GTC AGA GCA TCT TTG ATC GAG AAG CTA ATG AAA GAA AAA AGA AAG ATG AAG AGA AAT CAA
             2704        2713        2722        2731        2740        2749

V   A   S   P   Q   I   M   Q   R   M   S   A   V   N   F   E   T   I  STOP
         GTA GCA AGC CCT CAA ATA ATG CAA AGG ATG AGT GCA GTG AAT TTC GAA ACT ATA TAA GGA
             2764        2773        2782        2791        2800        2809

ACA ATG AAC TCA TCT GCC CTA GAG AGA ATG ACC CAG TGC ACG GTG CTG ATG GAA AGT TCT
             2824        2833        2842        2851        2860        2869

ATA CAA ACA AGT GCT CAC TGT GCA GAG CTG TCT TTC TAA CAG AAG CTT TGG AAA GGG CAA
             2884        2893        2902        2911        2920        2929

AGC TTC AAG AAA AAC CAT CCC ATG TTA GAG CTT CTC AAG AGG AAG ACA GCC CAG ACT CTT
             2944        2953        2962        2971        2980        2989

TCA GTT CTC TGG ATT CTG AGA TGT GCA AAG ACT ACC GAG TAT TGC CCA GGA TAG GCT ATC
             3004        3013        3022        3031        3040        3049

TTT GTC CAA AGG ATT TAA ACC CTG TCT GTG GTG ACG ATG GCC AAA CCT ACA ACA ATC CTT
             3064        3073        3082        3091        3100        3109

GCA TGC TCT GTC ATG AAA ACC TGA TAC GCC AAA CAA ATA CAC ACA TCC GCA GTA CAG GGA
             3124        3133        3142        3151        3160        3169

AGT GTG AGG AGA GCA GCA CCC CAG GAA CCA CCG CAG CCA GCA TGC CCC CGT TTG ACG AAT
             3184        3193        3202        3211        3220        3229

GAC ACG AAG ATT GTT GAA AGC CAT GAG GGA AAA AAT AAA CCC CAG TTT TGA ATC ACC TAC
             3244        3253        3262        3271        3280        3289

CTT CAC CAT CTG TAT ATA CAA AGA ATT TTT CGG AGC TTG TTT TAT TTG CTA TAG AAA ACA
             3304        3313        3322        3331        3340        3349

ATA CAG AGC TTT TGG GAA TGG AAT CAC TGA TTT TCA GTC TTT TCC ATT TCT TTC CTC CTA
             3364        3373        3382        3391        3400        3409

GAA TCT GTG ATC TGA GGG TAT AAA GAC ATT TCC ACC AAG TTT GAG CCC TCA AAA TGT CCT
             3424        3433        3442        3451        3460        3469
                                                  polyadenylation signal
         GAT TAC AAT GCT GTC TGT CCA ACT GCC TGT TCA ATA AAA GTA AAC TCA GCA GAA AA  ···
             3484        3493        3502        3511        3520        3529

······· poly(A) tail
```

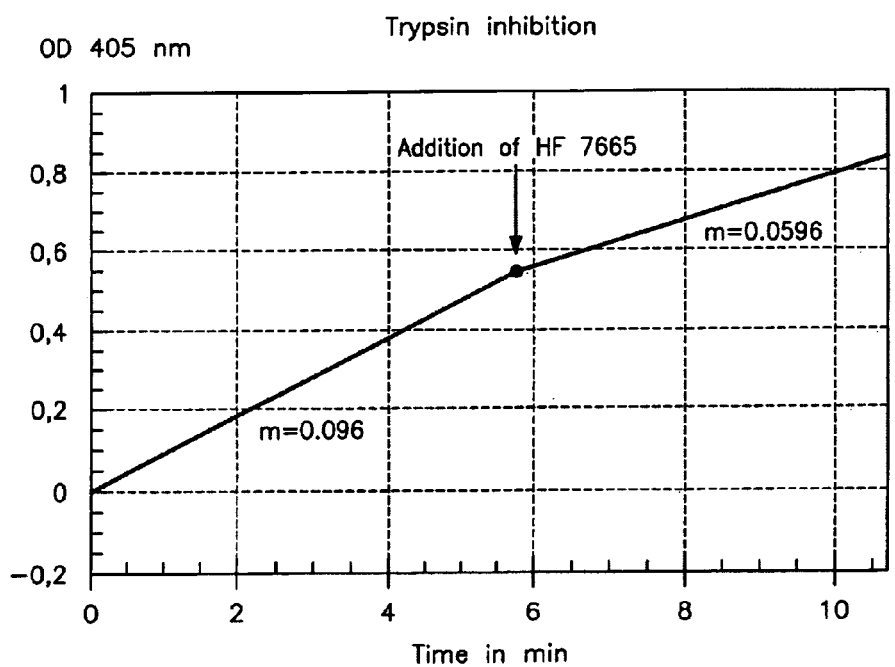

SERINE PROTEINASE INHIBITORS

The present invention relates to serine protease inhibitors, cDNA coding for serine protease inhibitors, medicaments containing such inhibitors or their coding nucleic acid, use of the compounds according to the invention for the preparation of medicaments for the treatment of various indications, antibodies or antibody fragments against epitopes of the compounds according to the invention, poly- or oligonucleotides which will hybridize to genes of the compounds according to the invention, a diagnostic agent for detecting the compounds according to the invention, and medicaments containing antibodies or poly- or oligonucleotides according to the invention.

Proteolytic processes play an important physiological role in all organisms; a distinction has to be made between non-specific and specific proteolytic reactions. The former include, for example, the digestion of food in the digestive tract by endopeptidases, and the intracellular degradation of used endogenous substances and phagocytosed materials by lysosomal proteases. Specific proteolyses mostly serve for the conversion of a proenzyme to its active form, as in the conversion of trypsinogen to trypsin, and of chymotrypsinogen to chymotrypsin, and in the callicrein-kinin cascades and the blood clotting cascade. Depending on the structure of the reactive site of the proteinases involved, they are classified into the classes of serine proteases (e.g., chymotrypsin, trypsin, elastase and cathepsin G), aspartate proteases (e.g., cathepsin D, cathepsin E and pepsin), cysteine proteases (e.g., cathepsin B, cathepsin H and cathepsin L), and the metallo-proteases (e.g., collagenase and thermolysin).

In order to be able to correct the proteolytic processes which often proceed in a cascade, the organisms is provided with a number of other proteins, the protease inhibitors (for a survey, see Laskowski and Kato, 1980, and Bode and Huber, 1992). Thus, the liver-synthesized human plasma protease inhibitors $\alpha_1$-antichymotrypsin and $\alpha_1$-proteinase inhibitors protect the lung tissue from non-specific attack by the proteinases cathepsin G and elastase from polymorphonu-clear lymphocytes. When the balance between proteases and their specific inhibitors is disturbed, pathological effects may arise. For example, an excess ratio of elastase to $\alpha_1$-proteinase inhibitor increases the risk of formation of a lung emphysema by a factor of about 20 to 30 in patients with a genetically caused deficiency in this factor as compared to the normal population (Carrel and Owen, 1980). With smokers, the formation of an emphysema is promoted by oxidation of the amino acid methionine which is present in the reactive site of the $\alpha_1$-proteinase inhibitor by oxidants contained in cigarette smoke (Miller and Kuschner, 1969; Ohisson et al., 1980). Also in the case of infection with Gram-negative bacteria, their endotoxins can cause disintegration of phagocytes and thus the secretion of lysosomal proteases, which may cause an uncontrolled damage to tissues and inflammations due to the increased consumption of protease inhibitors. For this reason, certain protease inhibitors have a high therapeutic potential (see, e.g., Fritz, 1980).

SUMMARY OF THE INVENTION

It has been the object of the present invention to provide further inhibitors of serine proteases. In addition, the genes or cDNA coding for the inhibitors according to the invention should be provided.

A specific feature of the serine protease inhibitors according to the invention is that the serine protease inhibitor has a domain with four cysteines, and a sequence of 0 to 20 amino acids is present between the first and second cysteines, or the serine protease inhibitor has a domain with six cysteines, and a sequence of 7 to 20 amino acids is present between the first and second cysteines.

BRIEF DESCRIPTION OF THE DRAWINGS

FIG. 1 illustrates VAKTI-1 cDNA and its translation product.

FIG. 2 illustrates VAKTI-2 cDNA and its translation product

FIG. 3 graphically illustrates trypsin inhibition using and embodiment of the subject invention.

DETAILED DESCRIPTION OF THE INVENTION

Preferably, a sequence of 13 amino acids is present between a first and a second cysteine, and/or a sequence of 18 amino acids is present between a second and a third cysteine, and/or a sequence of 2 amino acids is present between a third and a fourth cysteine.

It is particularly preferred that the sequence between a first and a second cysteine be selected from
HEFQAFMKNGKLF, SEYRKSRKNGRLF, DDFKKGERDGDFI, SEFRDQVRNGTLI, SAFRPFVRNGRLG, SEYRHYVRNGRLP, KEYEKQVRNGRLF, DEFRRLLQNGKLF, SQYQNQAKNGILF, AEYREQMKNGRLS, or NEYRKLVRNGKLA, DEFRSQMKNGKLI and/or the sequence between a second and a third cysteine be selected from
PQDKKFFQSLDGIMFINK, TRENDPIQGPDGKMHGNT,
TRENDPVLGPDGKTHGNK, TREHNPVRGPDGKMHGNK,
TRESDPVRGPDGRMHGNK, TRENDPIEGLDGKIHGNT,
TRENDPIRGPDGKMHGNL, TRENDPVRGPDGKTHGNK,
TRENDPIQGPDGKVHGNT, TRESDPVRDADGKSYNNQ, or
TRESDPVRGPDGKTHGNK and/or the sequence between a third and a fourth cysteine be selected from
AT, AL, AM, SM, or TM.

It is particularly preferred that the serine protease inhibitor according to the invention correspond to one of the following formulas:

$R_1$-C-HEFQAFMKNGKLF-C-PQDKKFFQSLDG-IMFINK-C-AT-C-$R_2$ (SEQ ID NO:30)

$R_1$-C-DDFKKGERDGDFI-C-PDYYEAVCGTDFK-TYDNR-C-AL-C-$R_2$ (SEQ ID NO:31)

$R_1$-C-SAFRPFVRNGRLG-C-TRENDPVLGPDGK-THGNK-C-AM-C-$R_2$ (SEQ ID NO:32)

$R_1$-C-KEYEKQVRNGRLF-C-TRESDPVRGP-DGRMHGNK-C-AL-C-$R_2$ (SEQ ID NO:33)

$R_1$-C-SQYQNQAKNGILF-C-TRENDPIRGPDGKM-HGNL-C-SM-C-$R_2$ (SEQ ID NO:34)

R₁-C-NEYRKLVRNGKLA-C-TRENDPIQGP-
DGKVHGNT-C-SM-C-R₂ (SEQ ID NO:35)

R₁-C-SEYRKSRKNGRLF-C-TRENDPIQGPDGKM-
HGNT-C-SM-C-R₂ (SEQ ID NO:36)

R₁-C-SEFRDQVRNGTLI-C-TREHNPVRGPDGKM-
HGNK-C-AM-C-R₂ (SEQ ID NO:37)

R₁-C-DEFRSQMKNGKLI-C-TRESDPVRGPDGK-
THGNK-C-TM-C-R₂, wherein $R_1$ is $NH_2$, an amino acid, or a peptide with up to 100 amino acids, and $R_2$ is COOH, $CONH_2$, an amino acid, or a peptide with up to 100 amino acids.

It is further preferred that the serine protease inhibitor contains one or more disulfide bridges. It is particularly for it to contain a disulfide bridge between the first and fourth cysteines and/or between the second and third cysteines, or to contain a disulfide bridge between the first and fifth cysteines and/or between the second and fourth cysteines and/or between the third and sixth cysteines.

Preferred representatives of the serine protease inhibitors according to the invention are the compounds HF 6479 and HF 7665, and fragments of proteins VAKTI-1 and VAKTI-2 according to FIGS. 1 and 2.

In addition to the amino acid sequence of the preferred compounds according to the invention, further information about the cDNA coding for the compounds according to the invention can also be seen from FIGS. 1 to 3. In particular, the corresponding motives and primer-hybridizing sites are indicated.

Compound HF 3479 according to the invention has a mass of 6,479 Dalton, and that of HF 7665 is 7,665 Dalton; both have been purified from hemofiltrate.

According to the invention, a cDNA coding for the compounds according to the invention, especially a cDNA having the nucleic acid sequence according to FIGS. 1 to 2, is also claimed.

The compounds according to the invention are useful as medicaments. In this case, they are administered together with pharmaceutically acceptable vehicles.

The medicaments according to the invention containing the protease inhibitors according to the invention are preferably administered in amounts of from 1 to 100 mg/kg of the patient's body weight. As the dosage form, all galenic formulations for peptide active substances may be used. The medicaments containing nucleic acids according to the invention are preferably administered in amounts of from 0.1 to 100 mg/kg of body weight of a corresponding patient. In this case, the galenic dosage forms which may be used are those which are suitable for the administration of nucleic acids without rendering the nucleic acids ineffective by metabolic influences before they have reached their site of action. For example, liposomes in which the nucleic acids are contained can be employed as a galenic dosage form.

The compounds according to the invention can be used, in particular, for the treatment of acute or chronic cervix inflammations, inflammations of Bartholin's gland or other vaginal regions, tonsillitis, pharyngitis and laryngitis, acute or chronic inflammatory processes accompanied by excessive formation of mucus and the resulting acute emergency situations, postoperative bleedings due to hyperfibrinolysis, and for the prophylaxis of lung emphysema formation in deficiencies of $\alpha_1$-proteinase inhibitor.

The compounds according to the invention can be administered in deficiencies of serine protease inhibitors to correct endogenous defects. The nucleic acids may also be used in gene therapy, either directly or coupled to suitable vehicles. Suitable vectors include, in particular, attenuated adenoviruses into which the corresponding genes have been incorporated.

The polypeptides according to the invention, especially VAKTI-I and VAKTI-II, can serve for the preparation of antibodies or antibody fragments. These are simply prepared by the immunization of appropriate mammals. By per se known operations, the antibodies may also be humanized so that such antibodies can also be employed for therapeutic use. Antibodies or antibody fragments can then by employed for the regulation of diseases in which the protease inhibitors are expressed in a pathological way. Also, antisense nucleic acids complementary to the nucleic acids according to the invention may also be employed in therapeutical use in overexpressions of the protease inhibitor genes.

The compounds according to the invention can be easily prepared by per se known methods of peptide or nucleotide synthesis. Preparation of the compounds by genetic engineering is also possible.

Those skilled in the art will recognize that fragments of the polypeptides according to the invention may also be used provided that they retain the inhibitory properties of the serine protease inhibitors. Those skilled in the art know how to find such fragments. Thus, this may be accomplished, for example, by a selected enzymatic cleavage of the compounds according to the invention. Side-chain modified amino acids may also be employed. N- or C-terminally modified polypeptides may also be used. In particular, phosphorylated, glycosylated, methylated, acetylated or similarly modified polypeptides can be employed provided that they do not substantially affect the activity of the serine protease inhibitors.

Derivatives of the nucleic acids according to the invention which have modified triplet structures in accordance with codon usage may also be used. In addition, nucleic acids according to the invention also include those which are more stable towards degradation by nucleases as compared with the native compounds, for example, the corresponding SODN derivatives usually employed in antisense technology to give the antisense structures a more stable design towards enzymatic attack.

Structures homologous to the polypeptides may also be used. In particular, these include polypeptide structures in which amino acids have been exchanged. Thus, for example, conservative amino acid substitutions in highly conserved regions can be considered as follows: any isoleucine, valine and leucine amino acid can be exchanged for any other of these amino acids, aspartate can be exchanged for glutamate and vice versa, glutamine for asparagine and vice versa, serine for threonine and vice versa. Conservative amino acid substitutions in less highly conserved regions can be as follows: Any of the amino acids isoleucine, valine and leucine for any other of these amino acids, aspartate for glutamate and vice versa, glutamine for asparagine and vice versa, serine for threonine and vice versa, glycine for alanine and vice versa, alanine for valine and vice versa, any of the amino acids leucine, isoleucine or valine for methionine, lysine for arginine and vice versa, either of the amino acids arginine or lysine for either of the amino acids aspartate or glutamate, either of the amino acids arginine or lysine for histidine, glutamine for glutamate and vice versa, and asparagine for aspartate and vice versa.

The mode of action of the peptides according to the invention will be illustrated by the following Example.

EXAMPLE

Measurement of Protease Inhibition by HF 7665

Measuring Composition:
84 µl measuring buffer (0.1 M HEPES, pH 7.5; 0.5 M NaCl)
1 µl trypsin (1 mg/ml in 1 mM HCl, 20 mM $CaCl_2$)
5 µL-BABNA (6 mg/ml N-α-benzoyl-L-arginine-p-nitroanilide hydrochloride)
10 µl protease inhibitor (10 µM or 75 µg/ml HF 7665 in $H_2O$)

The reaction was started by adding the chromogenic substrate, and the substrate conversion was followed by a photometer at X=405 nm. After about five minutes, 10 µl of protease inhibitor or the corresponding controls were added and the further course of the absorbance observed.

It could be shown that HF 7665 has an inhibitory effect on trypsin in a final concentration of about 1 µM or 7.5 µg/ml. Control experiments with corresponding amounts of BSA (7.5 µg/ml) and acetonitrile/TFA (0.8% ACN/0.001% TFA) did not show any trypsin inhibition. Further, an inhibitory effect of HF 7665 on chymotrypsin could not be observed in a similar test.

FIG. 3 shows that the substrate conversion is reduced by about 30% due to trypsin inhibition after the addition of HF 7665.

---

The invention claimed is:

1. A purified, synthesized, or genetically engineered serine protease inhibitor, characterized by having a domain with four cysteines, and a sequence of 13 amino acids is present between the first and second cysteines, a sequence of 18 amino acids is present between the second and third cysteines, and a sequence of 2 amino acids is present between the third and fourth cysteines.

2. The serine protease inhibitor according to claim 1, characterized in that the sequence of the domain between the first and second cysteines is selected from

HEFQAFMKNGKLF (SEQ ID NO: 7), SEYRK-SRKNGRLF (SEQ ID NO: 8),

DDFKKGERDGDFI (SEQ ID NO: 9), SEFRDQVRNGTLI (SEQ ID NO: 10),

SAFRPFVRNGRLG (SEQ ID NO: 11), SEYRHYVRNGRLP (SEQ ID NO: 12),

KEYEKQVRNGRLF (SEQ ID NO: 13), DEFRRLLQNGKLF (SEQ ID NO: 14),

SQYQNQAKNGILF (SEQ ID NO: 15), AEYREQMKNGRLS (SEQ ID NO: 16), or

NEYRKLVRNGKLA (SEQ ID NO: 17), DEFRSQMKNGKLI (SEQ ID NO: 18).

3. The serine protease inhibitor according to claim 1, characterized in that the sequence between the second and third cysteines is selected from

PQDKKFFQSLDGIMFINK (SEQ ID NO: 19), TRENDPIQGPDGKMHGNT (SEQ ID NO: 20,

TRENDPVLGPDGKTHGNK (SEQ ID NO: 21), TREHNPVRGPDGKMHGNK (SEQ ID NO: 22),

TRESDPVRGPDGRMHGNK (SEQ ID NO: 23), TRENDPIEGLDGKIHGNT (SEQ ID NO: 24),

TRENDPIRGPDGKMHGNL (SEQ ID NO: 25), TRENDPVRGPDGKTHGNK (SEQ ID NO: 26),

TRENDPIQGPDGKVHGNT (SEQ ID NO: 27), TRESDPVRDADGKSYNNQ (SEQ ID NO: 28), or TRESDPVRGPDGKTHGNK (SEQ ID NO: 29).

4. The serine protease inhibitor according to claim 1, characterized in that the sequence between the third and fourth cysteines of the domain is selected from AT, AL, AM, SM, or TM.

5. The serine protease inhibitor according to claim 1, having one of the following formulas:

$R_1$-C-HEFQAFMKNGKLF-C-PQDKKFFQSLDG-IMFINK-C-AT-C-$R_2$ (SEQ ID NO: 30)

$R_1$-C-DDFKKGERDGDFI-C-PDYYEAVCGTDGK-TYDNR-C-AL-C-$R_2$ (SEQ INO: 31)

$R_1$-C-SAFRPFVRGLG-G-TRENDPVLGPDGKTH-GNK-C-AM-C-$R_2$ (SEQ ID NO: 32)

$R_1$-C-KEYEKQVRNGRLF-C-TRESDPVRGP-DGRMHGNK-C-AL-C-$R_2$ (SEQ ID NO: 33)

$R_1$-C-SQYQNQAKNGILF-C-TRENDPIRGPDGKM-HGNL-C-SM-C-$R_2$ (SEQ ID NO: 34)

$R_1$-C-NEYRKLVRNGKLA-C-TRENDPIQGP-DGKVHGNT-C-SM-C-$R_2$ (SEQ D NO: 35)

$R_1$-C-SEYRKSRKNGRLF-C-TRENDPIQGPDGKM-HGNT-C-SM-C-$R_2$ (SEQ ID NO: 36)

$R_1$-SERDQVRNGTLI-C-TREHNPVRGPDGKMH-GNK-C-AM-C-$R_2$ (SEQ ID NO: 37)

$R_1$-C-SEYRHYVRNGRLP-C-TRENDPIEGLDGKI-HGNT-C-SM-C-$R_2$ (SEQ ID NO: 38)

$R_1$-C-DEFRRLLQNGKLF-C-TRENDPVRGPDGK-THGNK-C-AM-C-$R_2$ (SEQ ID NO: 39)

R₁-C-AEYREQMKNGRLS-C-TRESD-
PVRDADGKSYNNQ-C-TM-C-R₂ (SEQ NO: 40)
R₁-C-DERSQMGKLI-C-TRESDPVRGPDGKTHGNK-
C-TM-C-R₂ (SEQ ID NO: 41),
wherein R₁ is NH₂, an amino acid, or a peptide with up to 1000 amino acids, and R₂ is COOH, CONH₂, an amino acid, or a peptide with up to 1000 amino acids.

6. The serine protease inhibitor according to claim 1, characterized by containing
- a disulfide bridge between the first and fourth cysteines and/or between the second and third cysteines; or
- a disulfide bridge between the first and a fifth cysteine and/or between the second and fourth cysteines and/or between the third and a sixth cysteine.

7. The serine protease inhibitor according to claim 1, characterized by being a fragment of VAKTI-1 (SEQ. ID. NO. 1) or VAKTI-2 (SEQ. ID. NO. 2).

8. A purified, synthesized or genetically engineered serine protease inhibitor, characterized by being HF 6479 (SEQ. ID. NO. 3) or HF 7665 (SEQ. ID. NO. 4).

9. A medicament containing
the serine protease inhibitor according to claim 8
together with a pharmaceutical vehicle.

10. The medicament according to claim 9, containing from 0.01 to 1000 mg per kg of body weight of the serine protease inhibitor.

11. Method of using the medicament according to claim 9, wherein the medicament is the serine protease inhibitor, for the treatment of acute or chronic cervix inflammations, inflammations of Bartholin's glands and other vaginal regions, tonsillitis, pharyngitis and laryngitis, acute or chronic inflammatory processes accompanied by excessive formation of mucus and the resulting acute emergency situations, postoperative bleeding due to hyperfibrinolysis, and for the prophylaxis of lung emphysema formation in deficiencies of $\alpha_1$-proteinase inhibitor.

* * * * *

SEQUENCE LISTING

<160> NUMBER OF SEQ ID NOS: 25

<210> SEQ ID NO 1
<211> LENGTH: 387
<212> TYPE: DNA
<213> ORGANISM: Mus musculus

<400> SEQUENCE: 1

```
ctgatttgca gcctgtggtg ggagagaact cgccagcctg tggaagaaga cgcagcgcgc        60
tacacagcaa cccggaacca accaggcatt ccgcagcaca tcccgtctgc tccagaagag       120
gtcttagaag tgagggctgt gacccttccg atcctgagcg gctagttttc aaacctccct       180
tgcccctgct tccttctggc tcaggctgct cctccttagg actttgtggg tccagttttg       240
ccttctgttc tgatggtgat tagcggctca cctccagcgc ttcttcctgt ttcccaggac       300
cacccagagg ctaaggaatc agtcattccc tgttgccttc tccaggaagg caggctaagg       360
gttctgaggt gactgagaaa aatgttt                                           387
```

<210> SEQ ID NO 2
<211> LENGTH: 353
<212> TYPE: DNA
<213> ORGANISM: Mus musculus

<400> SEQUENCE: 2

```
cgcggcgccc agcgaggcag agcgctgtcg catcccgggc gtccaccgc catgggctc         60 tcctggagcc cgcgacctcc actgctgatg atcctgctac tggtgctgtc gttgtggctg      120
ccacttggag caggaaactc ccttgccaca gagaacaggt ttgtgaacag ctgtacccag      180
gccagaaaga aatgcgaggc taatcccgct tgcaaggctg cctaccagca cctgggctcc      240
tgcacctcca gttaagcagg ccgctgccct tagaggagtc tgccatgtct gcagactgcc      300
tagaggcagc agaacaactc aggaacagct ctctgataga ctgcaggtgc cat             353
```

<210> SEQ ID NO 3
<211> LENGTH: 498
<212> TYPE: DNA
<213> ORGANISM: Mus musculus

<400> SEQUENCE: 3

```
aattcggaac gagggtgaag gagcttcgca agtcccaagg ccctttggaa gtcgctgaag        60
ctgccgtcag ccaatccagt ggactcgcag ccaaatttgt catccactgt cacatccccc      120
agtgggactc cgacaaatgt gaagaacagc tggaagagac catcaaaaac tgcctgtctg      180
cagcagagga caagaagctt aaatccgtcg ccttcccacc gttccccagt ggcagaaact      240
```

-continued

| | |
|---|---|
| gcttccccaa acagacggcc gcccaggtga ccctcaaggc catctcggct cacttcgacg | 300 |
| actcgagctc gtcctcgctg aagaatgtgt acttcctgct cttcgacagc gagacatcgg | 360 |
| catctacgtg caggagatgg ccaaactgga caccaagtag ctctctccag tggcggcgaa | 420 |
| ggaggaggat cggcgtgacg tcacaagagc gggggtttta ttttttacaa ggattgcaga | 480 |
| agggtgacgg ggcatggg | 498 |

<210> SEQ ID NO 4
<211> LENGTH: 1935
<212> TYPE: DNA
<213> ORGANISM: Mus musculus

<400> SEQUENCE: 4

| | |
|---|---|
| gaatttggcc ctcgaggcca agaattcggc acgaggcgcg gcgcccagcg caggcagagc | 60 |
| gctgtcgcat cccgggcgtc cacccgccat ggggctctcc tggagcccgc gacctccact | 120 |
| gctgatgatc ctgctactgg tgctgtcgtt gtggctgcca cttggagcag gaaactccct | 180 |
| tgccacagag aacaggtttg tgaacagctg tacccaggcc agaaagaaat gcgaggctaa | 240 |
| tcccgcttgc aaggctgcct accagcacct gggctcctgc acctccagtt taagcaggcc | 300 |
| gctgccctta gaggagtctg ccatgtctgc agactgccta gaggcagcag aacaactcag | 360 |
| gaacagctct ctgatagact gcaggtgcca tcggcgcatg aagcaccaag ctacctgtct | 420 |
| ggacatttat tggaccgttc accctgcccg aagccttggt gactacgagt ggatgtctc | 480 |
| accctatgaa gacacagtga ccagcaaacc ctggaaaatg aatcttagca agttgaacat | 540 |
| gctcaaacca gactcggacc tctgcctcaa atttgctatg ctgtgtactc ttcacgacaa | 600 |
| gtgtgaccgc ctgcgcaagg cctacgggga ggcatgctca gggatccgct gccagcgcca | 660 |
| cctctgccta gcccagctgc gctccttctt tgagaaggca gcagagtccc acgctcaggg | 720 |
| tctgctgctg tgtccctgtg caccagaaga tgcgggctgt ggggagcggc ggcgtaacac | 780 |
| catcgccccc agttgcgccc tgccttctgt aaccccccaat tgcctggatc tgcggagctt | 840 |
| ctgccgtgcg gacccttgt gcagatcacg cctgatggac ttccagaccc actgtcatcc | 900 |
| tatggacatc cttgggactt gtgcaactga gcagtccaga tgtctgcggg catacctggg | 960 |
| gctgattggg actgccatga ccccaaactt catcagcaag gtcaacacta ctgttgcctt | 1020 |
| aagctgcacc tgccgaggca gcggcaacct acaggacgag tgtgaacagc tggaaaggtc | 1080 |
| cttctcccag aacccctgcc tcgtggaggc cattgcagct aagatgcgtt tccacagaca | 1140 |
| gctcttctcc caggactggg cagactctac tttttcagtg gtgcagcagc agaacagcaa | 1200 |
| ccctgctctg agactgcagc ccaggctacc cattctttct ttctccatcc ttcccttgat | 1260 |
| tctgctgcag accctctggt agctgggctt cctcagggtc cttttgtcctc tccaccacac | 1320 |
| ccagactgat ttgcagcctg tggtgggaga gaactcgcca gcctgtggaa gaagacgcag | 1380 |
| cgtgctacac agcaacccgg aaccaaccag gcattccgca gcacatcccg tctgctccag | 1440 |
| aagaggtctt agaagtgagg gctgtgaccc ttccgatcct gagcggctag ttttcaaacc | 1500 |
| tcccttgccc ctgcttcctt ctggctcagg ctgctcctcc ttaggacttt gtgggtccag | 1560 |
| ttttgccttc tgttctgatg gtgattagcg gctcacctcc agcgcttctt cctgtttccc | 1620 |
| aggaccaccc agaggctaag gaatcagtca ttccctgttg ccttctccag gaaggcaggc | 1680 |
| taagggttct gaggtgactg agaaaaatgt ttcctttgtg tggaaggctg gtgctccagc | 1740 |
| ctccacgtcc ctctgaatgg aagataaaaa cctgctggtg tcttgactgc tctgccaggc | 1800 |
| aatcctgaac atttgggcat gaagagctaa agtctttggg tcttgtttaa ctcctattac | 1860 | tgtccccaaa ttcccctagt cccttgggtc atgattaaac attttgactt aaaaaaaaaa     1920 aaaaaaaaaa aaaaa                                                      1935

<210> SEQ ID NO 5
<211> LENGTH: 397
<212> TYPE: PRT
<213> ORGANISM: Mus musculus

<400> SEQUENCE: 5

```
Met Gly Leu Ser Trp Ser Pro Arg Pro Leu Leu Met Ile Leu Leu
 1               5                  10                  15

Leu Val Leu Ser Leu Trp Leu Pro Leu Gly Ala Gly Asn Ser Leu Ala
             20                  25                  30

Thr Glu Asn Arg Phe Val Asn Ser Cys Thr Gln Ala Arg Lys Lys Cys
         35                  40                  45

Glu Ala Asn Pro Ala Cys Lys Ala Ala Tyr Gln His Leu Gly Ser Cys
     50                  55                  60

Thr Ser Ser Leu Ser Arg Pro Leu Pro Leu Glu Glu Ser Ala Met Ser
 65                  70                  75                  80

Ala Asp Cys Leu Glu Ala Ala Glu Gln Leu Arg Asn Ser Ser Leu Ile
                 85                  90                  95

Asp Cys Arg Cys His Arg Arg Met Lys His Gln Ala Thr Cys Leu Asp
            100                 105                 110

Ile Tyr Trp Thr Val His Pro Ala Arg Ser Leu Gly Asp Tyr Glu Leu
        115                 120                 125

Asp Val Ser Pro Tyr Glu Asp Thr Val Thr Ser Lys Pro Trp Lys Met
    130                 135                 140

Asn Leu Ser Lys Leu Asn Met Leu Lys Pro Asp Ser Asp Leu Cys Leu
145                 150                 155                 160

Lys Phe Ala Met Leu Cys Thr Leu His Asp Lys Cys Asp Arg Leu Arg
                165                 170                 175

Lys Ala Tyr Gly Glu Ala Cys Ser Gly Ile Arg Cys Gln Arg His Leu
            180                 185                 190

Cys Leu Ala Gln Leu Arg Ser Phe Phe Glu Lys Ala Ala Glu Ser His
        195                 200                 205

Ala Gln Gly Leu Leu Cys Pro Cys Ala Pro Glu Asp Ala Gly Cys
    210                 215                 220

Gly Glu Arg Arg Arg Asn Thr Ile Ala Pro Ser Cys Ala Leu Pro Ser
225                 230                 235                 240

Val Thr Pro Asn Cys Leu Asp Leu Arg Ser Phe Cys Arg Ala Asp Pro
                245                 250                 255

Leu Cys Arg Ser Arg Leu Met Asp Phe Gln Thr His Cys His Pro Met
            260                 265                 270

Asp Ile Leu Gly Thr Cys Ala Thr Glu Gln Ser Arg Cys Leu Arg Ala
        275                 280                 285

Tyr Leu Gly Leu Ile Gly Thr Ala Met Thr Pro Asn Phe Ile Ser Lys
    290                 295                 300

Val Asn Thr Thr Val Ala Leu Ser Cys Thr Cys Arg Gly Ser Gly Asn
305                 310                 315                 320

Leu Gln Asp Glu Cys Glu Gln Leu Glu Arg Ser Phe Ser Gln Asn Pro
                325                 330                 335

Cys Leu Val Glu Ala Ile Ala Ala Lys Met Arg Phe His Arg Gln Leu
            340                 345                 350
```

```
Phe Ser Gln Asp Trp Ala Asp Ser Thr Phe Ser Val Val Gln Gln Gln
            355                 360                 365

Asn Ser Asn Pro Ala Leu Arg Leu Gln Pro Arg Leu Pro Ile Leu Ser
            370                 375                 380

Phe Ser Ile Leu Pro Leu Ile Leu Leu Gln Thr Leu Trp
385                 390                 395

<210> SEQ ID NO 6
<211> LENGTH: 460
<212> TYPE: PRT
<213> ORGANISM: Homo sapiens

<400> SEQUENCE: 6

Met Phe Leu Ala Thr Leu Tyr Phe Ala Leu Pro Leu Leu Asp Leu Leu
  1               5                  10                  15

Leu Ser Ala Glu Val Ser Gly Gly Asp Arg Leu Asp Cys Val Lys Ala
             20                  25                  30

Ser Asp Gln Cys Leu Lys Glu Gln Ser Cys Ser Thr Lys Tyr Arg Thr
         35                  40                  45

Leu Arg Gln Cys Val Ala Gly Lys Glu Thr Asn Phe Ser Leu Ala Ser
     50                  55                  60

Gly Leu Glu Ala Lys Asp Glu Cys Arg Ser Ala Met Glu Ala Leu Lys
 65                  70                  75                  80

Gln Lys Ser Leu Tyr Asn Cys Arg Cys Lys Arg Gly Met Lys Lys Glu
                 85                  90                  95

Lys Asn Cys Leu Arg Ile Tyr Trp Ser Met Tyr Gln Ser Leu Gln Gly
            100                 105                 110

Asn Asp Leu Leu Glu Asp Ser Pro Tyr Glu Pro Val Asn Ser Arg Leu
            115                 120                 125

Ser Asp Ile Phe Arg Val Val Pro Phe Ile Ser Val Glu His Ile Pro
        130                 135                 140

Lys Gly Asn Asn Cys Leu Asp Ala Ala Lys Ala Cys Asn Leu Asp Asp
145                 150                 155                 160

Ile Cys Lys Lys Tyr Arg Ser Ala Tyr Ile Thr Pro Cys Thr Thr Ser
                165                 170                 175

Val Ser Asn Asp Val Cys Asn Arg Arg Lys Cys His Lys Ala Leu Arg
            180                 185                 190

Gln Phe Phe Asp Lys Val Pro Ala Lys His Ser Tyr Gly Met Leu Phe
        195                 200                 205

Cys Ser Cys Arg Asp Ile Ala Cys Thr Glu Arg Arg Arg Gln Thr Ile
    210                 215                 220

Val Pro Val Cys Ser Tyr Glu Glu Arg Glu Lys Pro Asn Cys Leu Asn
225                 230                 235                 240

Leu Gln Asp Ser Cys Lys Thr Asn Tyr Ile Cys Arg Ser Arg Leu Ala
                245                 250                 255

Asp Phe Phe Thr Asn Cys Gln Pro Glu Ser Arg Ser Val Ser Ser Cys
            260                 265                 270

Leu Lys Glu Asn Tyr Ala Asp Cys Leu Leu Ala Tyr Ser Gly Leu Ile
        275                 280                 285

Gly Thr Val Met Thr Pro Asn Tyr Ile Asp Ser Ser Ser Leu Ser Val
    290                 295                 300

Ala Pro Trp Cys Asp Cys Ser Asn Ser Gly Asn Asp Leu Glu Glu Cys
305                 310                 315                 320

Leu Lys Phe Leu Asn Phe Phe Lys Asp Asn Thr Cys Leu Lys Asn Ala
                325                 330                 335
```

```
Ile Gln Ala Phe Gly Asn Gly Ser Asp Val Thr Val Trp Gln Pro Ala
            340                 345                 350

Phe Pro Val Gln Thr Thr Thr Ala Thr Thr Thr Ala Leu Arg Val
            355                 360                 365

Lys Asn Lys Pro Leu Gly Pro Ala Gly Ser Glu Asn Glu Ile Pro Thr
            370                 375                 380

His Val Leu Pro Pro Cys Ala Asn Leu Gln Ala Gln Lys Leu Lys Ser
385                 390                 395                 400

Asn Val Ser Gly Asn Thr His Leu Cys Ile Ser Asn Gly Asn Tyr Glu
            405                 410                 415

Lys Glu Gly Leu Gly Ala Ser Ser His Ile Thr Thr Lys Ser Met Ala
            420                 425                 430

Ala Pro Pro Ser Cys Gly Leu Ser Pro Leu Val Leu Val Val Thr
            435                 440                 445

Ala Leu Ser Thr Leu Leu Ser Leu Thr Glu Thr Ser
450                 455                 460

<210> SEQ ID NO 7
<211> LENGTH: 464
<212> TYPE: PRT
<213> ORGANISM: Homo sapiens

<400> SEQUENCE: 7

Met Ile Leu Ala Asn Val Phe Phe Leu Phe Phe Phe Leu Asp Glu Thr
1               5                   10                  15

Leu Arg Ser Leu Ala Ser Pro Ser Ser Leu Gln Asp Pro Glu Leu His
            20                  25                  30

Gly Trp Arg Pro Pro Val Asp Cys Val Arg Ala Asn Glu Leu Cys Ala
            35                  40                  45

Ala Glu Ser Asn Cys Ser Ser Arg Tyr Arg Thr Leu Arg Gln Cys Leu
            50                  55                  60

Ala Gly Arg Asp Arg Asn Thr Met Leu Ala Asn Lys Glu Cys Gln Ala
65                  70                  75                  80

Ala Leu Glu Val Leu Gln Glu Ser Pro Leu Tyr Asp Cys Arg Cys Lys
            85                  90                  95

Arg Gly Met Lys Lys Glu Leu Gln Cys Leu Gln Ile Tyr Trp Ser Ile
            100                 105                 110

His Leu Gly Leu Thr Glu Gly Glu Glu Phe Tyr Glu Ala Ser Pro Tyr
            115                 120                 125

Glu Pro Val Thr Ser Arg Leu Ser Asp Ile Phe Arg Leu Ala Ser Ile
            130                 135                 140

Phe Ser Gly Thr Gly Ala Asp Pro Val Val Ser Ala Lys Ser Asn His
145                 150                 155                 160

Cys Leu Asp Ala Ala Lys Ala Cys Asn Leu Asn Asp Asn Cys Lys Lys
            165                 170                 175

Leu Arg Ser Ser Tyr Ile Ser Ile Cys Asn Arg Glu Ile Ser Pro Thr
            180                 185                 190

Glu Arg Cys Asn Arg Arg Lys Cys His Lys Ala Leu Arg Gln Phe Phe
            195                 200                 205

Asp Arg Val Pro Ser Glu Tyr Thr Tyr Arg Met Leu Phe Cys Ser Cys
            210                 215                 220

Gln Asp Gln Ala Cys Ala Glu Arg Arg Gln Thr Ile Leu Pro Ser
225                 230                 235                 240

Cys Ser Tyr Glu Asp Lys Glu Lys Pro Asn Cys Leu Asp Leu Arg Gly
```

-continued

```
                245                 250                 255
Val Cys Arg Thr Asp His Leu Cys Arg Ser Arg Leu Ala Asp Phe His
                260                 265                 270

Ala Asn Cys Arg Ala Ser Tyr Gln Thr Val Thr Ser Cys Pro Ala Asp
                275                 280                 285

Asn Tyr Gln Ala Cys Leu Gly Ser Tyr Ala Gly Met Ile Gly Phe Asp
                290                 295                 300

Met Thr Pro Asn Tyr Val Asp Ser Ser Pro Thr Gly Ile Val Val Ser
305                 310                 315                 320

Pro Trp Cys Ser Cys Arg Gly Ser Gly Asn Met Glu Glu Cys Glu
                325                 330                 335

Lys Phe Leu Arg Asp Phe Thr Glu Asn Pro Cys Leu Arg Asn Ala Ile
                340                 345                 350

Gln Ala Phe Gly Asn Gly Thr Asp Val Asn Val Ser Pro Lys Gly Pro
                355                 360                 365

Ser Phe Gln Ala Thr Gln Ala Pro Arg Val Glu Lys Thr Pro Ser Leu
                370                 375                 380

Pro Asp Asp Leu Ser Asp Ser Thr Ser Leu Gly Thr Ser Val Ile Thr
385                 390                 395                 400

Thr Cys Thr Ser Val Gln Glu Gln Gly Leu Lys Ala Asn Asn Ser Lys
                405                 410                 415

Glu Leu Ser Met Cys Phe Thr Glu Leu Thr Thr Asn Ile Ile Pro Gly
                420                 425                 430

Ser Asn Lys Val Ile Lys Pro Asn Ser Gly Pro Ser Arg Ala Arg Pro
                435                 440                 445

Ser Ala Ala Leu Thr Val Leu Ser Val Leu Met Leu Lys Leu Ala Leu
                450                 455                 460
```

<210> SEQ ID NO 8
<211> LENGTH: 468
<212> TYPE: PRT
<213> ORGANISM: Rattus norvegicus

<400> SEQUENCE: 8

```
Met Phe Leu Ala Thr Leu Tyr Phe Ala Leu Pro Leu Leu Asp Leu Leu
1               5                   10                  15

Met Ser Ala Glu Val Ser Gly Gly Asp Arg Leu Asp Cys Val Lys Ala
                20                  25                  30

Ser Asp Gln Cys Leu Lys Glu Gln Ser Cys Ser Thr Lys Tyr Arg Thr
            35                  40                  45

Leu Arg Gln Cys Val Ala Gly Lys Glu Thr Asn Phe Ser Leu Thr Ser
50                  55                  60

Gly Leu Glu Ala Lys Asp Glu Cys Arg Ser Ala Met Glu Ala Leu Lys
65                  70                  75                  80

Gln Lys Ser Leu Tyr Asn Cys Arg Cys Lys Arg Gly Met Lys Lys Glu
                85                  90                  95

Lys Asn Cys Leu Arg Ile Tyr Trp Ser Met Tyr Gln Ser Leu Gln Gly
                100                 105                 110

Asn Asp Leu Leu Glu Asp Ser Pro Tyr Glu Pro Val Asn Ser Arg Leu
            115                 120                 125

Ser Asp Ile Phe Arg Ala Val Pro Phe Ile Ser Asp Val Phe Gln Gln
            130                 135                 140

Val Glu His Ile Ser Lys Gly Asn Asn Cys Leu Asp Ala Ala Lys Ala
145                 150                 155                 160
```

```
Cys Asn Leu Asp Asp Thr Cys Lys Lys Tyr Arg Ser Ala Tyr Ile Thr
            165                 170                 175

Pro Cys Thr Thr Ser Met Ser Asn Glu Val Cys Asn Arg Arg Lys Cys
            180                 185                 190

His Lys Ala Leu Arg Gln Phe Phe Asp Lys Val Pro Ala Lys His Ser
            195                 200                 205

Tyr Gly Met Leu Phe Cys Ser Cys Arg Asp Ile Ala Cys Thr Glu Arg
            210                 215                 220

Arg Arg Gln Thr Ile Val Pro Val Cys Ser Tyr Glu Glu Arg Glu Arg
225                 230                 235                 240

Pro Asn Cys Leu Ser Leu Gln Asp Ser Cys Lys Thr Asn Tyr Ile Cys
            245                 250                 255

Arg Ser Arg Leu Ala Asp Phe Phe Thr Asn Cys Gln Pro Glu Ser Arg
            260                 265                 270

Ser Val Ser Asn Cys Leu Lys Glu Asn Tyr Ala Asp Cys Leu Leu Ala
            275                 280                 285

Tyr Ser Gly Leu Ile Gly Thr Val Met Thr Pro Asn Tyr Val Asp Ser
            290                 295                 300

Ser Ser Leu Ser Val Ala Pro Trp Cys Asp Cys Ser Asn Ser Gly Asn
305                 310                 315                 320

Asp Leu Glu Asp Cys Leu Lys Phe Leu Asn Phe Phe Lys Asp Asn Thr
            325                 330                 335

Cys Leu Lys Asn Ala Ile Gln Ala Phe Gly Asn Gly Ser Asp Val Thr
            340                 345                 350

Met Trp Gln Pro Ala Pro Val Gln Thr Thr Thr Ala Thr Thr Thr
            355                 360                 365

Thr Ala Phe Arg Val Lys Asn Lys Pro Leu Gly Pro Ala Gly Ser Glu
            370                 375                 380

Asn Glu Ile Pro Thr His Val Leu Pro Pro Cys Ala Asn Leu Gln Ala
385                 390                 395                 400

Gln Lys Leu Lys Ser Asn Val Ser Gly Ser Thr His Leu Cys Leu Ser
            405                 410                 415

Asp Ser Asp Phe Gly Lys Asp Gly Leu Ala Gly Ala Ser Ser His Ile
            420                 425                 430

Thr Thr Lys Ser Met Ala Ala Pro Pro Ser Cys Ser Leu Ser Ser Leu
            435                 440                 445

Pro Val Leu Met Leu Thr Ala Leu Ala Ala Leu Leu Ser Val Ser Leu
            450                 455                 460

Ala Glu Thr Ser
465

<210> SEQ ID NO 9
<211> LENGTH: 464
<212> TYPE: PRT
<213> ORGANISM: Rattus Norvegicus

<400> SEQUENCE: 9

Met Ile Leu Ala Asn Ala Phe Cys Leu Phe Phe Phe Leu Asp Glu Thr
1               5                   10                  15

Leu Arg Ser Leu Ala Ser Pro Ser Ser Leu Gln Gly Ser Glu Leu His
            20                  25                  30

Gly Trp Arg Pro Gln Val Asp Cys Val Arg Ala Asn Glu Leu Cys Ala
            35                  40                  45

Ala Glu Ser Asn Cys Ser Ser Arg Tyr Arg Thr Leu Arg Gln Cys Leu
        50                  55                  60
```

```
Ala Gly Arg Asp Arg Asn Thr Met Leu Ala Asn Lys Glu Cys Gln Ala
 65                  70                  75                  80

Ala Leu Glu Val Leu Gln Glu Ser Pro Leu Tyr Asp Cys Arg Cys Lys
             85                  90                  95

Arg Gly Met Lys Lys Glu Leu Gln Cys Leu Gln Ile Tyr Trp Ser Ile
            100                 105                 110

His Leu Gly Leu Thr Glu Gly Glu Phe Tyr Glu Ala Ser Pro Tyr
            115                 120                 125

Glu Pro Val Thr Ser Arg Leu Ser Asp Ile Phe Arg Leu Ala Ser Ile
    130                 135                 140

Phe Ser Gly Thr Gly Thr Asp Pro Ala Val Ser Thr Lys Ser Asn His
145                 150                 155                 160

Cys Leu Asp Ala Ala Lys Ala Cys Asn Leu Asn Asp Asn Cys Lys Lys
                165                 170                 175

Leu Arg Ser Ser Tyr Ile Ser Ile Cys Asn Arg Glu Ile Ser Pro Thr
            180                 185                 190

Glu Arg Cys Asn Arg Arg Lys Cys His Lys Ala Leu Arg Gln Phe Phe
            195                 200                 205

Asp Arg Val Pro Ser Glu Tyr Thr Tyr Arg Met Leu Phe Cys Ser Cys
    210                 215                 220

Gln Asp Gln Ala Cys Ala Glu Arg Arg Gln Thr Ile Leu Pro Ser
225                 230                 235                 240

Cys Ser Tyr Glu Asp Lys Glu Lys Pro Asn Cys Leu Asp Leu Arg Ser
                245                 250                 255

Leu Cys Arg Thr Asp His Leu Cys Arg Ser Arg Leu Ala Asp Phe His
            260                 265                 270

Ala Asn Cys Arg Ala Ser Tyr Arg Thr Ile Thr Ser Cys Pro Ala Asp
            275                 280                 285

Asn Tyr Gln Ala Cys Leu Gly Ser Tyr Ala Gly Met Ile Gly Phe Asp
    290                 295                 300

Met Thr Pro Asn Tyr Val Asp Ser Asn Pro Thr Gly Ile Val Val Ser
305                 310                 315                 320

Pro Trp Cys Asn Cys Arg Gly Ser Gly Asn Met Glu Glu Cys Glu
                325                 330                 335

Lys Phe Leu Arg Asp Phe Thr Glu Asn Pro Cys Leu Arg Asn Ala Ile
            340                 345                 350

Gln Ala Phe Gly Asn Gly Thr Asp Val Asn Met Ser Pro Lys Gly Pro
            355                 360                 365

Ser Leu Pro Ala Thr Gln Ala Pro Arg Val Glu Lys Thr Pro Ser Leu
    370                 375                 380

Pro Asp Asp Leu Ser Asp Ser Thr Ser Leu Gly Thr Ser Val Ile Thr
385                 390                 395                 400

Thr Cys Thr Ser Ile Gln Glu Gln Gly Leu Lys Ala Asn Asn Ser Lys
                405                 410                 415

Glu Leu Ser Met Cys Phe Thr Glu Leu Thr Thr Asn Ile Ser Pro Gly
            420                 425                 430

Ser Lys Lys Val Ile Lys Leu Asn Ser Gly Ser Ser Arg Ala Arg Leu
            435                 440                 445

Ser Ala Ala Leu Thr Ala Leu Pro Leu Leu Met Leu Thr Leu Ala Leu
450                 455                 460

<210> SEQ ID NO 10
<211> LENGTH: 282
```

```
<212> TYPE: DNA
<213> ORGANISM: Homo sapiens
<220> FEATURE:
<221> NAME/KEY: unsure
<222> LOCATION: (0)...(0)
<223> OTHER INFORMATION: n = A, T, C or G

<400> SEQUENCE: 10
gcgctgnntg ncngnangng ggggcgggag gtgccggtcg agggagcccc gctctcagag      60
ctccagggga ggagcgangg gagcgcggag cccggccgcc tacagctcgc catggtgcgc     120
cccctgaacc cgcgaccgct gccgcccgta gnnnnnnnnn nnnnnnnnnn nnnnnnnnnn     180
nnnnnnnngc tctcgcagcc ggagaccccc ttcccacag aaagccgact catgaacagc     240
tgtctccagg ccaggaggaa gtgccaggct gatcccacct gc                        282

<210> SEQ ID NO 11
<211> LENGTH: 20
<212> TYPE: DNA
<213> ORGANISM: Homo sapiens

<400> SEQUENCE: 11
gcctctcgca gccggagacc                                                  20

<210> SEQ ID NO 12
<211> LENGTH: 21
<212> TYPE: DNA
<213> ORGANISM: Homo sapiens

<400> SEQUENCE: 12
caggtgggat cagcctggca c                                                21

<210> SEQ ID NO 13
<211> LENGTH: 41
<212> TYPE: DNA
<213> ORGANISM: Homo sapiens

<400> SEQUENCE: 13
tctcgcagcc ggagaccccc ttcccacaga aagccgactc a                          41

<210> SEQ ID NO 14
<211> LENGTH: 1792
<212> TYPE: DNA
<213> ORGANISM: Homo sapiens

<400> SEQUENCE: 14
atggtgcgcc ccctgaaccc gcgaccgctg ccgcccgtag tcctgatgtt gctgctgctg      60
ctgccgccgt cgccgctgcc tctcgcagcc ggagaccccc ttcccacaga aagccgactc     120
atgaacagct gtctccaggc caggaggaag tgccaggctg atcccacctg cagtgctgcc     180
taccaccacc tggattcctg cacctctagc ataagcaccc cactgccctc agaggagcct     240
tcggtccctg ctgactgcct ggaggcagca cagcaactca ggaacagctc tctgataggc     300
tgcatgtgcc accggcgcat gaagaaccag gttgcctgct tggacatcta ttggaccgtt     360
caccgtgccc gcagccttgg taactatgag ctggatgtct cccctatga agacacagtg     420 accagcaaac cctggaaaat gaatctcagc aaactgaaca tgctcaaacc agactcagac     480
ctctgcctca gtttgccat gctgtgtact ctcaatgaca agtgtgaccg gctgcgcaag     540
gcctacgggg aggcgtgctc cgggcccac tgccagcgcc acgtctgcct caggcagctg     600
ctcactttct tcgagaaggc cgccgagccc acgcgcagg gcctgctact gtgcccatgt     660
```

```
gcccccaacg accggggctg cggggagcgc cggcgcaaca ccatcgcccc caactgcgcg     720
ctgccgcctg tggcccccaa ctgcctggag ctgcggcgcc tctgcttctc cgacccgctt     780
tgcagatcac gcctggtgga tttccagacc cactgccatc ccatggacat cctaggaact     840
tgtgcaacag agcagtccag atgtctacga gcatacctgg ggctgattgg gactgccatg     900 accccaact  ttgtcagcaa tgtcaacacc agtgttgcct taagctgcac ctgccgaggc     960
agtggcaacc tgcaggagga gtgtgaaatg ctggaagggt tcttctccca caaccccctgc    1020 ctcacggagg ccattgcagc taagatgcgt tttcacagcc aactcttctc ccaggactgg    1080
ccacacccta cctttgctgt gatggcacac cagaatgaaa accctgctgt gaggccacag    1140
ccctgggtgc cctctctttt ctcctgcacg cttcccttga ttctgctcct gagcctatgg    1200
tagctggact tccccagggc cctcttcccc tccaccacac ccaggtggac ttgcagccca    1260 caagggtga  ggaaaggaca gcagcaggaa ggaggtgcag tgcgcagatg agggcacagg    1320
agaagctaag ggttatgacc tccagatcct tactggtcca gtcctcattc cctccacccc    1380
atctccactt ctgattcatg ctgcccctcc ttggtggcca caatttagcc atgtcatctg    1440
gtggtgacca gctccaccaa gcccctttct gagcccttcc tcttgactac caggatcacc    1500
agaatctaat aagttagcct ttctctattg cattccagat tagggttagg gtagggagga    1560
ctgggtgttc tgaggcagcc tagaaagtca ttctccttg tgaagaaggc tcctgccccc    1620
tcgtctcctc ctctgagtgg aggatggaaa actactgcct gcactgccct gtccccggat    1680
cctgccgaac atctgggcat caggagctgg agcctgtggg ccttgcttta ttcctattat    1740
tgtcctaaag tctctctggg ctcttggatc atgattaaac ctttgactta ag            1792
```

<210> SEQ ID NO 15
<211> LENGTH: 400
<212> TYPE: PRT
<213> ORGANISM: Homo Sapiens

<400> SEQUENCE: 15

```
Met Val Arg Pro Leu Asn Pro Arg Pro Leu Pro Pro Val Val Leu Met
 1               5                   10                  15

Leu Leu Leu Leu Leu Pro Pro Ser Pro Leu Pro Leu Ala Ala Gly Asp
             20                  25                  30

Pro Leu Pro Thr Glu Ser Arg Leu Met Asn Ser Cys Leu Gln Ala Arg
         35                  40                  45

Arg Lys Cys Gln Ala Asp Pro Thr Cys Ser Ala Ala Tyr His His Leu
     50                  55                  60

Asp Ser Cys Thr Ser Ser Ile Ser Thr Pro Leu Pro Ser Glu Glu Pro
 65                  70                  75                  80

Ser Val Pro Ala Asp Cys Leu Glu Ala Ala Gln Gln Leu Arg Asn Ser
                 85                  90                  95

Ser Leu Ile Gly Cys Met Cys His Arg Arg Met Lys Asn Gln Val Ala
            100                 105                 110

Cys Leu Asp Ile Tyr Trp Thr Val His Arg Ala Arg Ser Leu Gly Asn
        115                 120                 125

Tyr Glu Leu Asp Val Ser Pro Tyr Glu Asp Thr Val Thr Ser Lys Pro
    130                 135                 140

Trp Lys Met Asn Leu Ser Lys Leu Asn Met Leu Lys Pro Asp Ser Asp
145                 150                 155                 160

Leu Cys Leu Lys Phe Ala Met Leu Cys Thr Leu Asn Asp Lys Cys Asp
                165                 170                 175
```

```
Arg Leu Arg Lys Ala Tyr Gly Glu Ala Cys Ser Gly Pro His Cys Gln
                180                 185                 190

Arg His Val Cys Leu Arg Gln Leu Leu Thr Phe Phe Glu Lys Ala Ala
            195                 200                 205

Glu Pro His Ala Gln Gly Leu Leu Leu Cys Pro Cys Ala Pro Asn Asp
        210                 215                 220

Arg Gly Cys Gly Glu Arg Arg Asn Thr Ile Ala Pro Asn Cys Ala
225                 230                 235                 240

Leu Pro Pro Val Ala Pro Asn Cys Leu Glu Leu Arg Arg Leu Cys Phe
                245                 250                 255

Ser Asp Pro Leu Cys Arg Ser Arg Leu Val Asp Phe Gln Thr His Cys
            260                 265                 270

His Pro Met Asp Ile Leu Gly Thr Cys Ala Thr Glu Gln Ser Arg Cys
        275                 280                 285

Leu Arg Ala Tyr Leu Gly Leu Ile Gly Thr Ala Met Thr Pro Asn Phe
    290                 295                 300

Val Ser Asn Val Asn Thr Ser Val Ala Leu Ser Cys Thr Cys Arg Gly
305                 310                 315                 320

Ser Gly Asn Leu Gln Glu Glu Cys Glu Met Leu Glu Gly Phe Phe Ser
                325                 330                 335

His Asn Pro Cys Leu Thr Glu Ala Ile Ala Ala Lys Met Arg Phe His
            340                 345                 350

Ser Gln Leu Phe Ser Gln Asp Trp Pro His Pro Thr Phe Ala Val Met
        355                 360                 365

Ala His Gln Asn Glu Asn Pro Ala Val Arg Pro Gln Pro Trp Val Pro
    370                 375                 380

Ser Leu Phe Ser Cys Thr Leu Pro Leu Ile Leu Leu Ser Leu Trp
385                 390                 395                 400

<210> SEQ ID NO 16
<211> LENGTH: 1837
<212> TYPE: DNA
<213> ORGANISM: Homo sapeins

<400> SEQUENCE: 16
cccaggaccc tggtgggaga gtgtgtgcgt cgcgctggag ggcgggaggc ggggcggga       60 ggtgccggtc gagggagccc cgctctcaga gctccagggg aggagcgagg ggagcgcgga     120
gcccggcgcc tacagctcgc catggtgcgc ccctgaacc gcgaccgct gccgcccgta      180 gtcctgatgt tgctgctgct gctgccgccg tcgccgctgc ctctcgcagc cggagacccc    240
cttcccacag aaagccgact catgaacagc tgtctccagg ccaggaggaa gtgccaggct    300
gatcccacct gcagtgctgc ctaccaccac ctggattcct gcacctctag cataagcacc    360
ccactgccct cagaggagcc ttcggtccct gctgactgcc tggaggcagc acagcaactc    420
aggaacagct ctctgatagg ctgcatgtgc accggcgca tgaagaacca ggttgcctgc    480
ttggacatct attggaccgt tcaccgtgcc cgcagccttg actcagacct ctgcctcaag    540
tttgccatgc tgtgtactct caatgacaag tgtgaccggc tgcgcaaggc ctacggggag    600
gcgtgctccg ggccccactg ccagcgccac gtctgcctca gcagctgct cactttcttc     660 gagaaggccg ccgagcccca cgcgcagggc ctgctactgt gcccatgtgc ccccaacgac    720
cggggctgcg gggagcgccg gcgcaacacc atcgccccca actgcgcgct gccgcctgtg    780
gcccccaact gcctggagct gcggcgcctc tgcttctccg acccgctttg cagatcacgc    840
ctggtggatt tccagaccca ctgccatccc atggacatcc taggaacttg tgcaacagag    900
```

```
cagtccagat gtctacgagc atacctgggg ctgattggga ctgccatgac ccccaacttt      960
gtcagcaatg tcaacaccag tgttgcctta agctgcacct gccgaggcag tggcaacctg     1020
caggaggagt gtgaaatgct ggaagggttc ttctcccaca acccctgcct cacggaggcc     1080
attgcagcta agatgcgttt tcacagccaa ctcttctccc aggactggcc acaccctacc     1140
tttgctgtga tggcacacca gaatgaaaac cctgctgtga ggccacagcc ctgggtgccc     1200
tctcttttct cctgcacgct tcccttgatt ctgctcctga gcctatggta gctggacttc     1260
cccagggccc tcttcccctc caccacaccc aggtggactt gcagcccaca aggggtgagg     1320
aaaggacagc agcaggaagg aggtgcagtg cgcagatgag ggcacaggag aagctaaggg     1380
ttatgacctc cagatcctta ctggtccagt cctcattccc tccacccat ctccacttct      1440
gattcatgct gcccctcctt ggtggccaca atttagccat gtcatctggt ggtgaccagc     1500
tccaccaagc ccctttctga gcccttcctc ttgactacca ggatcaccag aatctaataa     1560
gttagccttt ctctattgca ttccagatta gggttagggt agggaggact gggtgttctg     1620
aggcagccta gaaagtcatt ctcctttgtg aagaaggctc ctgccccctc gtctcctcct    1680
ctgagtggag gatggaaaac tactgcctgc actgccctgt ccccggatcc tgccgaacat    1740
ctgggcatca ggagctggag cctgtgggcc ttgctttatt cctattattg tcctaaagtc    1800
tctctgggct cttggatcat gattaaacct ttgactt                              1837
```

<210> SEQ ID NO 17
<211> LENGTH: 369
<212> TYPE: PRT
<213> ORGANISM: Homo sapiens

<400> SEQUENCE: 17

```
Met Val Arg Pro Leu Asn Pro Arg Pro Leu Pro Pro Val Val Leu Met
  1               5                  10                  15

Leu Leu Leu Leu Pro Pro Ser Pro Leu Pro Leu Ala Ala Gly Asp
             20                  25                  30

Pro Leu Pro Thr Glu Ser Arg Leu Met Asn Ser Cys Leu Gln Ala Arg
         35                  40                  45

Arg Lys Cys Gln Ala Asp Pro Thr Cys Ser Ala Ala Tyr His His Leu
     50                  55                  60

Asp Ser Cys Thr Ser Ser Ile Ser Thr Pro Leu Pro Ser Glu Glu Pro
 65                  70                  75                  80

Ser Val Pro Ala Asp Cys Leu Glu Ala Ala Gln Gln Leu Arg Asn Ser
                 85                  90                  95

Ser Leu Ile Gly Cys Met Cys His Arg Met Lys Asn Gln Val Ala
             100                 105                 110

Cys Leu Asp Ile Tyr Trp Thr Val His Arg Ala Arg Ser Leu Asp Ser
         115                 120                 125

Asp Leu Cys Leu Lys Phe Ala Met Leu Cys Thr Leu Asn Asp Lys Cys
     130                 135                 140

Asp Arg Leu Arg Lys Ala Tyr Gly Glu Ala Cys Ser Gly Pro His Cys
145                 150                 155                 160

Gln Arg His Val Cys Leu Arg Gln Leu Leu Thr Phe Phe Glu Lys Ala
                 165                 170                 175

Ala Glu Pro His Ala Gln Gly Leu Leu Leu Cys Pro Cys Ala Pro Asn
             180                 185                 190

Asp Arg Gly Cys Gly Glu Arg Arg Asn Thr Ile Ala Pro Asn Cys
         195                 200                 205
```

```
Ala Leu Pro Pro Val Ala Pro Asn Cys Leu Glu Leu Arg Arg Leu Cys
    210                 215                 220

Phe Ser Asp Pro Leu Cys Arg Ser Arg Leu Val Asp Phe Gln Thr His
225                 230                 235                 240

Cys His Pro Met Asp Ile Leu Gly Thr Cys Ala Thr Glu Gln Ser Arg
                245                 250                 255

Cys Leu Arg Ala Tyr Leu Gly Leu Ile Gly Thr Ala Met Thr Pro Asn
            260                 265                 270

Phe Val Ser Asn Val Asn Thr Ser Val Ala Leu Ser Cys Thr Cys Arg
        275                 280                 285

Gly Ser Gly Asn Leu Gln Glu Glu Cys Glu Met Leu Glu Gly Phe Phe
    290                 295                 300

Ser His Asn Pro Cys Leu Thr Glu Ala Ile Ala Ala Lys Met Arg Phe
305                 310                 315                 320

His Ser Gln Leu Phe Ser Gln Asp Trp Pro His Pro Thr Phe Ala Val
                325                 330                 335

Met Ala His Gln Asn Glu Asn Pro Ala Val Arg Pro Gln Pro Trp Val
            340                 345                 350

Pro Ser Leu Phe Ser Cys Thr Leu Pro Leu Ile Leu Leu Leu Ser Leu
        355                 360                 365

Trp

<210> SEQ ID NO 18
<211> LENGTH: 628
<212> TYPE: PRT
<213> ORGANISM: Artificial Sequence
<220> FEATURE:
<223> OTHER INFORMATION: Chimeric receptor comprising human sequence.

<400> SEQUENCE: 18

Met Val Arg Pro Leu Asn Pro Arg Pro Leu Pro Pro Val Val Leu Met
1               5                   10                  15

Leu Leu Leu Leu Leu Pro Pro Ser Pro Leu Pro Leu Ala Ala Gly Asp
            20                  25                  30

Pro Leu Pro Thr Glu Ser Arg Leu Met Asn Ser Cys Leu Gln Ala Arg
        35                  40                  45

Arg Lys Cys Gln Ala Asp Pro Thr Cys Ser Ala Ala Tyr His His Leu
    50                  55                  60

Asp Ser Cys Thr Ser Ser Ile Ser Thr Pro Leu Pro Ser Glu Glu Pro
65                  70                  75                  80

Ser Val Pro Ala Asp Cys Leu Glu Ala Ala Gln Gln Leu Arg Asn Ser
                85                  90                  95

Ser Leu Ile Gly Cys Met Cys His Arg Arg Met Lys Asn Gln Val Ala
            100                 105                 110

Cys Leu Asp Ile Tyr Trp Thr Val His Arg Ala Arg Ser Leu Gly Asn
        115                 120                 125

Tyr Glu Leu Asp Val Ser Pro Tyr Glu Asp Thr Val Thr Ser Lys Pro
    130                 135                 140

Trp Lys Met Asn Leu Ser Lys Leu Asn Met Leu Lys Pro Asp Ser Asp
145                 150                 155                 160

Leu Cys Leu Lys Phe Ala Met Leu Cys Thr Leu Asn Asp Lys Cys Asp
                165                 170                 175

Arg Leu Arg Lys Ala Tyr Gly Glu Ala Cys Ser Gly Pro His Cys Gln
            180                 185                 190
```

-continued

```
Arg His Val Cys Leu Arg Gln Leu Leu Thr Phe Phe Glu Lys Ala Ala
    195                 200                 205

Glu Pro His Ala Gln Gly Leu Leu Cys Pro Cys Ala Pro Asn Asp
210                 215                 220

Arg Gly Cys Gly Glu Arg Arg Asn Thr Ile Ala Pro Asn Cys Ala
225                 230                 235                 240

Leu Pro Pro Val Ala Pro Asn Cys Leu Glu Leu Arg Arg Leu Cys Phe
                245                 250                 255

Ser Asp Pro Leu Cys Arg Ser Arg Leu Val Asp Phe Gln Thr His Cys
                260                 265                 270

His Pro Met Asp Ile Leu Gly Thr Cys Ala Thr Glu Gln Ser Arg Cys
            275                 280                 285

Leu Arg Ala Tyr Leu Gly Leu Ile Gly Thr Ala Met Thr Pro Asn Phe
    290                 295                 300

Val Ser Asn Val Asn Thr Ser Val Ala Leu Ser Cys Thr Cys Arg Gly
305                 310                 315                 320

Ser Gly Asn Leu Gln Glu Cys Glu Met Leu Glu Gly Phe Phe Ser
                325                 330                 335

His Asn Pro Cys Leu Thr Glu Ala Ile Ala Ala Lys Met Arg Phe His
                340                 345                 350

Ser Gln Leu Phe Ser Gln Asp Trp Pro His Pro Thr Phe Ala Val Met
            355                 360                 365

Ala His Gln Asn Glu Asn Pro Ala Val Arg Pro Gln Pro Trp Val Pro
    370                 375                 380

Ser Leu Phe Ser Cys Thr Leu Pro Leu Ile Leu Leu Ser Leu Trp
385                 390                 395                 400

Pro Asp Lys Thr His Thr Cys Pro Pro Cys Pro Ala Pro Glu Leu Leu
                405                 410                 415

Gly Gly Pro Ser Val Phe Leu Phe Pro Pro Lys Pro Lys Asp Thr Leu
                420                 425                 430

Met Ile Ser Arg Thr Pro Glu Val Thr Cys Val Val Val Asp Val Ser
            435                 440                 445

His Glu Asp Pro Glu Val Lys Phe Asn Trp Tyr Val Asp Gly Val Glu
    450                 455                 460

Val His Asn Ala Lys Thr Lys Pro Arg Glu Glu Gln Tyr Asn Ser Thr
465                 470                 475                 480

Tyr Arg Val Val Ser Val Leu Thr Val Leu His Gln Asp Trp Leu Asn
                485                 490                 495

Gly Lys Glu Tyr Lys Cys Lys Val Ser Asn Lys Ala Leu Pro Ala Pro
                500                 505                 510

Ile Glu Lys Thr Ile Ser Lys Ala Lys Gly Gln Pro Arg Glu Pro Gln
            515                 520                 525

Val Tyr Thr Leu Pro Pro Ser Arg Glu Glu Met Thr Lys Asn Gln Val
    530                 535                 540

Ser Leu Thr Cys Leu Val Lys Gly Phe Tyr Pro Ser Asp Ile Ala Val
545                 550                 555                 560

Glu Trp Glu Ser Asn Gly Gln Pro Glu Asn Asn Tyr Lys Thr Thr Pro
                565                 570                 575

Pro Val Leu Asp Ser Asp Gly Ser Phe Phe Leu Tyr Ser Lys Leu Thr
                580                 585                 590

Val Asp Lys Ser Arg Trp Gln Gln Gly Asn Val Phe Ser Cys Ser Val
            595                 600                 605

Met His Glu Ala Leu His Asn His Tyr Thr Gln Lys Ser Leu Ser Leu
```

-continued

```
            610                 615                 620
Ser Pro Gly Lys
625

<210> SEQ ID NO 19
<211> LENGTH: 951
<212> TYPE: PRT
<213> ORGANISM: Artificial Sequence
<220> FEATURE:
<223> OTHER INFORMATION: Chimeric receptor comprising rat sequence.

<400> SEQUENCE: 19

Met Gly Gly Thr Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Leu Glu Pro Ser Ser Leu Gln Gly Ser Glu Leu
    50                  55                  60

His Gly Trp Arg Pro Gln Val Asp Cys Val Arg Ala Asn Glu Leu Cys
65                  70                  75                  80

Ala Ala Glu Ser Asn Cys Ser Ser Arg Tyr Arg Thr Leu Arg Gln Cys
                85                  90                  95

Leu Ala Gly Arg Asp Arg Asn Thr Met Leu Ala Asn Lys Glu Cys Gln
            100                 105                 110

Ala Ala Leu Glu Val Leu Gln Glu Ser Pro Leu Tyr Asp Cys Arg Cys
        115                 120                 125

Lys Arg Gly Met Lys Lys Glu Leu Gln Cys Leu Gln Ile Tyr Trp Ser
    130                 135                 140

Ile His Leu Gly Leu Thr Glu Gly Glu Glu Phe Tyr Glu Ala Ser Pro
145                 150                 155                 160

Tyr Glu Pro Val Thr Ser Arg Leu Ser Asp Ile Phe Arg Leu Ala Ser
                165                 170                 175

Ile Phe Ser Gly Thr Gly Thr Asp Pro Ala Val Ser Thr Lys Ser Asn
            180                 185                 190

His Cys Leu Asp Ala Ala Lys Ala Cys Asn Leu Asn Asp Asn Cys Lys
        195                 200                 205

Lys Leu Arg Ser Ser Tyr Ile Ser Ile Cys Asn Arg Glu Ile Ser Pro
    210                 215                 220

Thr Glu Arg Cys Asn Arg Arg Lys Cys His Lys Ala Leu Arg Gln Phe
225                 230                 235                 240

Phe Asp Arg Val Pro Ser Glu Tyr Thr Tyr Arg Met Leu Phe Cys Ser
                245                 250                 255

Cys Gln Asp Gln Ala Cys Ala Glu Arg Arg Arg Gln Thr Ile Leu Pro
            260                 265                 270

Ser Cys Ser Tyr Glu Asp Lys Glu Lys Pro Asn Cys Leu Asp Leu Arg
        275                 280                 285

Ser Leu Cys Arg Thr Asp His Leu Cys Arg Ser Arg Leu Ala Asp Phe
    290                 295                 300

His Ala Asn Cys Arg Ala Ser Tyr Arg Thr Ile Thr Ser Cys Pro Ala
305                 310                 315                 320

Asp Asn Tyr Gln Ala Cys Leu Gly Ser Tyr Ala Gly Met Ile Gly Phe
                325                 330                 335

Asp Met Thr Pro Asn Tyr Val Asp Ser Asn Pro Thr Gly Ile Val Val
```

-continued

```
                340                 345                 350
Ser Pro Trp Cys Asn Cys Arg Gly Ser Gly Asn Met Glu Glu Glu Cys
            355                 360                 365

Glu Lys Phe Leu Arg Asp Phe Thr Glu Asn Pro Cys Leu Arg Asn Ala
    370                 375                 380

Ile Gln Ala Phe Gly Asn Gly Thr Asp Val Asn Met Ser Pro Lys Gly
385                 390                 395                 400

Pro Ser Leu Pro Ala Thr Gln Ala Pro Arg Val Glu Lys Thr Pro Ser
                405                 410                 415

Leu Pro Asp Asp Leu Ser Asp Ser Thr Ser Leu Gly Thr Ser Val Ile
            420                 425                 430

Thr Thr Cys Thr Ser Ile Gln Glu Gln Gly Leu Lys Ala Asn Asn Ser
        435                 440                 445

Lys Glu Leu Ser Met Cys Phe Thr Glu Leu Thr Thr Asn Ile Ile Pro
    450                 455                 460

Gly Trp Arg Ala Trp Val Pro Val Val Leu Gly Val Leu Thr Ala Leu
465                 470                 475                 480

Val Thr Ala Ala Ala Leu Ala Leu Ile Leu Leu Arg Lys Arg Arg Lys
                485                 490                 495

Glu Thr Arg Phe Gly Gln Ala Phe Asp Ser Val Met Ala Arg Gly Glu
            500                 505                 510

Pro Ala Val His Phe Arg Ala Ala Arg Ser Phe Asn Arg Glu Arg Pro
        515                 520                 525

Glu Arg Ile Glu Ala Thr Leu Asp Ser Leu Gly Ile Ser Asp Glu Leu
    530                 535                 540

Lys Glu Lys Leu Glu Asp Val Leu Ile Pro Glu Gln Gln Phe Thr Leu
545                 550                 555                 560

Gly Arg Met Leu Gly Lys Gly Glu Phe Gly Ser Val Arg Glu Ala Gln
                565                 570                 575

Leu Lys Gln Glu Asp Gly Ser Phe Val Lys Val Ala Val Lys Met Leu
            580                 585                 590

Lys Ala Asp Ile Ile Ala Ser Ser Asp Ile Glu Glu Phe Leu Arg Glu
        595                 600                 605

Ala Ala Cys Met Lys Glu Phe Asp His Pro His Val Ala Lys Leu Val
    610                 615                 620

Gly Val Ser Leu Arg Ser Arg Ala Lys Gly Arg Leu Pro Ile Pro Met
625                 630                 635                 640

Val Ile Leu Pro Phe Met Lys His Gly Asp Leu His Ala Phe Leu Leu
                645                 650                 655

Ala Ser Arg Ile Gly Glu Asn Pro Phe Asn Leu Pro Leu Gln Thr Leu
            660                 665                 670

Ile Arg Phe Met Val Asp Ile Ala Cys Gly Met Glu Tyr Leu Ser Ser
        675                 680                 685

Arg Asn Phe Ile His Arg Asp Leu Ala Ala Arg Asn Cys Met Leu Ala
    690                 695                 700

Glu Asp Met Thr Val Cys Val Ala Asp Phe Gly Leu Ser Arg Lys Ile
705                 710                 715                 720

Tyr Ser Gly Asp Tyr Tyr Arg Gln Gly Cys Ala Ser Lys Leu Pro Val
                725                 730                 735

Lys Trp Leu Ala Leu Glu Ser Leu Ala Asp Asn Leu Tyr Thr Val Gln
            740                 745                 750

Ser Asp Val Trp Ala Phe Gly Val Thr Met Trp Glu Ile Met Thr Arg
        755                 760                 765
```

```
Gly Gln Thr Pro Tyr Ala Gly Ile Glu Asn Ala Glu Ile Tyr Asn Tyr
    770             775                 780
Leu Ile Gly Gly Asn Arg Leu Lys Gln Pro Pro Glu Cys Met Glu Asp
785             790                 795                 800
Val Tyr Asp Leu Met Tyr Gln Cys Trp Ser Ala Asp Pro Lys Gln Arg
                805                 810                 815
Pro Ser Phe Thr Cys Leu Arg Met Glu Leu Glu Asn Ile Leu Gly Gln
                820                 825                 830
Leu Ser Val Leu Ser Ala Ser Gln Asp Pro Leu Tyr Ile Asn Ile Glu
                835                 840                 845
Arg Ala Glu Glu Pro Thr Ala Gly Gly Ser Leu Glu Leu Pro Gly Arg
850                 855                 860
Asp Gln Pro Tyr Ser Gly Ala Gly Asp Gly Ser Gly Met Gly Ala Val
865                 870                 875                 880
Gly Gly Thr Pro Ser Asp Cys Arg Tyr Ile Leu Thr Pro Gly Gly Leu
                885                 890                 895
Ala Glu Gln Pro Gly Gln Ala Glu His Gln Pro Glu Ser Pro Leu Asn
                900                 905                 910
Glu Thr Gln Arg Leu Leu Leu Gln Gln Gly Leu Leu Pro His Ser
                915                 920                 925
Ser Cys Ala Asp Ala Ser Leu Lys Met Ala Asp Pro Asn Arg Phe Arg
930                 935                 940
Gly Lys Asp Leu Pro Val Leu
945                 950

<210> SEQ ID NO 20
<211> LENGTH: 888
<212> TYPE: PRT
<213> ORGANISM: Artificial Sequence
<220> FEATURE:
<223> OTHER INFORMATION: Chimeric receptor comprising murine sequence.

<400> SEQUENCE: 20

Met Gly Gly Thr Ala Ala Arg Leu Gly Ala Val Ile Leu Phe Val Val
1               5                   10                  15
Ile Val Gly Leu His Gly Val Arg Gly Lys Tyr Ala Leu Ala Asp Ala
                20                  25                  30
Ser Leu Lys Met Ala Asp Pro Asn Arg Phe Arg Gly Lys Asp Leu Pro
                35                  40                  45
Val Leu Asp Gln Leu Leu Glu Ala Gly Asn Ser Leu Ala Thr Glu Asn
            50                  55                  60
Arg Phe Val Asn Ser Cys Thr Gln Ala Arg Lys Lys Cys Glu Ala Asn
65                  70                  75                  80
Pro Ala Cys Lys Ala Ala Tyr Gln His Leu Gly Ser Cys Thr Ser Ser
                85                  90                  95
Leu Ser Arg Pro Leu Pro Leu Glu Glu Ser Ala Met Ser Ala Asp Cys
                100                 105                 110
Leu Glu Ala Ala Glu Gln Leu Arg Asn Ser Ser Leu Ile Asp Cys Arg
                115                 120                 125
Cys His Arg Arg Met Lys His Gln Ala Thr Cys Leu Asp Ile Tyr Trp
            130                 135                 140
Thr Val His Pro Ala Arg Ser Leu Gly Asp Tyr Glu Leu Asp Val Ser
145                 150                 155                 160
Pro Tyr Glu Asp Thr Val Thr Ser Lys Pro Trp Lys Met Asn Leu Ser
                165                 170                 175
```

-continued

```
Lys Leu Asn Met Leu Lys Pro Asp Ser Asp Leu Cys Leu Lys Phe Ala
                180                 185                 190
Met Leu Cys Thr Leu His Asp Lys Cys Asp Arg Leu Arg Lys Ala Tyr
            195                 200                 205
Gly Glu Ala Cys Ser Gly Ile Arg Cys Gln Arg His Leu Cys Leu Ala
        210                 215                 220
Gln Leu Arg Ser Phe Phe Glu Lys Ala Ala Glu Ser His Ala Gln Gly
225                 230                 235                 240
Leu Leu Leu Cys Pro Cys Pro Pro Glu Asp Ala Gly Cys Gly Glu Arg
                245                 250                 255
Arg Arg Asn Thr Ile Ala Pro Ser Cys Ala Leu Pro Ser Val Thr Pro
            260                 265                 270
Asn Cys Leu Asp Leu Arg Ser Phe Cys Arg Ala Asp Pro Leu Cys Arg
        275                 280                 285
Ser Arg Leu Met Asp Phe Gln Thr His Cys His Pro Met Asp Ile Leu
290                 295                 300
Gly Thr Cys Ala Thr Glu Gln Ser Arg Cys Leu Arg Ala Tyr Leu Gly
305                 310                 315                 320
Leu Ile Gly Thr Ala Met Thr Pro Asn Phe Ile Ser Lys Val Asn Thr
                325                 330                 335
Thr Val Ala Leu Ser Cys Thr Cys Arg Gly Ser Gly Asn Leu Gln Asp
            340                 345                 350
Glu Cys Glu Gln Leu Glu Arg Ser Phe Ser Gln Asn Pro Cys Leu Val
        355                 360                 365
Glu Ala Ile Ala Ala Lys Met Arg Phe His Arg Gln Leu Phe Ser Gln
370                 375                 380
Asp Trp Ala Asp Ser Thr Phe Ser Val Val Gln Gln Asn Ser Asn
385                 390                 395                 400
Pro Ala Trp Arg Ala Trp Val Pro Val Leu Gly Val Leu Thr Ala
                405                 410                 415
Leu Val Thr Ala Ala Leu Ala Leu Ile Leu Arg Lys Arg Arg
            420                 425                 430
Lys Glu Thr Arg Phe Gly Gln Ala Phe Asp Ser Val Met Ala Arg Gly
            435                 440                 445
Glu Pro Ala Val His Phe Arg Ala Ala Arg Ser Phe Asn Arg Glu Arg
        450                 455                 460
Pro Glu Arg Ile Glu Ala Thr Leu Asp Ser Leu Gly Ile Ser Asp Glu
465                 470                 475                 480
Leu Lys Glu Lys Leu Glu Asp Val Leu Ile Pro Glu Gln Gln Phe Thr
                485                 490                 495
Leu Gly Arg Met Leu Gly Lys Gly Glu Phe Gly Ser Val Arg Glu Ala
            500                 505                 510
Gln Leu Lys Gln Glu Asp Gly Ser Phe Val Lys Val Ala Val Lys Met
        515                 520                 525
Leu Lys Ala Asp Ile Ile Ala Ser Ser Asp Ile Glu Glu Phe Leu Arg
530                 535                 540
Glu Ala Ala Cys Met Lys Glu Phe Asp His Pro His Val Ala Lys Leu
545                 550                 555                 560
Val Gly Val Ser Leu Arg Ser Arg Ala Lys Gly Arg Leu Pro Ile Pro
                565                 570                 575
Met Val Ile Leu Pro Phe Met Lys His Gly Asp Leu His Ala Phe Leu
            580                 585                 590
```

```
Leu Ala Ser Arg Ile Gly Glu Asn Pro Phe Asn Leu Pro Leu Gln Thr
            595                 600                 605

Leu Ile Arg Phe Met Val Asp Ile Ala Cys Gly Met Glu Tyr Leu Ser
            610                 615                 620

Ser Arg Asn Phe Ile His Arg Asp Leu Ala Ala Arg Asn Cys Met Leu
625                 630                 635                 640

Ala Glu Asp Met Thr Val Cys Val Ala Asp Phe Gly Leu Ser Arg Lys
                645                 650                 655

Ile Tyr Ser Gly Asp Tyr Tyr Arg Gln Gly Cys Ala Ser Lys Leu Pro
                660                 665                 670

Val Lys Trp Leu Ala Leu Glu Ser Leu Ala Asp Asn Leu Tyr Thr Val
            675                 680                 685

Gln Ser Asp Val Trp Ala Phe Gly Val Thr Met Trp Glu Ile Met Thr
            690                 695                 700

Arg Gly Gln Thr Pro Tyr Ala Gly Ile Glu Asn Ala Glu Ile Tyr Asn
705                 710                 715                 720

Tyr Leu Ile Gly Gly Asn Arg Leu Lys Gln Pro Pro Glu Cys Met Glu
                725                 730                 735

Asp Val Tyr Asp Leu Met Tyr Gln Cys Trp Ser Ala Asp Pro Lys Gln
                740                 745                 750

Arg Pro Ser Phe Thr Cys Leu Arg Met Glu Leu Glu Asn Ile Leu Gly
            755                 760                 765

Gln Leu Ser Val Leu Ser Ala Ser Gln Asp Pro Leu Tyr Ile Asn Ile
            770                 775                 780

Glu Arg Ala Glu Glu Pro Thr Ala Gly Gly Ser Leu Glu Leu Pro Gly
785                 790                 795                 800

Arg Asp Gln Pro Tyr Ser Gly Ala Gly Asp Gly Ser Gly Met Gly Ala
                805                 810                 815

Val Gly Gly Thr Pro Ser Asp Cys Arg Tyr Ile Leu Thr Pro Gly Gly
                820                 825                 830

Leu Ala Glu Gln Pro Gly Gln Ala Glu His Gln Pro Glu Ser Pro Leu
            835                 840                 845

Asn Glu Thr Gln Arg Leu Leu Leu Gln Gln Gly Leu Leu Pro His
            850                 855                 860

Ser Ser Cys Ala Asp Ala Ser Leu Lys Met Ala Asp Pro Asn Arg Phe
865                 870                 875                 880

Arg Gly Lys Asp Leu Pro Val Leu
                885

<210> SEQ ID NO 21
<211> LENGTH: 37
<212> TYPE: DNA
<213> ORGANISM: Homo sapiens

<400> SEQUENCE: 21
gcgaggggag cgcggagccc ggcgcctaca gctcgcc                                37

<210> SEQ ID NO 22
<211> LENGTH: 20
<212> TYPE: DNA
<213> ORGANISM: Mus musculus

<400> SEQUENCE: 22
gcccgcgacc tccactgctg                                                   20

<210> SEQ ID NO 23
```

```
<211> LENGTH: 18
<212> TYPE: DNA
<213> ORGANISM: Mus musculus

<400> SEQUENCE: 23
ctgtggggag cggcggcg                                                18

<210> SEQ ID NO 24
<211> LENGTH: 20
<212> TYPE: DNA
<213> ORGANISM: Mus musculus

<400> SEQUENCE: 24
cctgaaccta tggtaactgg                                              20

<210> SEQ ID NO 25
<211> LENGTH: 17
<212> TYPE: DNA
<213> ORGANISM: Mus musculus

<400> SEQUENCE: 25
acccagtcct ccctacc                                                 17
```